United States Patent
Thomas et al.

(10) Patent No.: US 9,200,246 B2
(45) Date of Patent: Dec. 1, 2015

(54) CO-CULTURE DEVICE ASSEMBLY

(75) Inventors: Donald Thomas, San Diego, CA (US); Wei Li, Hangzhou (CN); Ning Ke, San Diego, CA (US); Nan Li, San Diego, CA (US); Adrian Papas, San Diego, CA (US); Manfred Watzele, Weilheim (DE); Alexander Seiler, Habach (DE); Tianxing Wang, Hangzhou (CN); Yama Abassi, San Diego, CA (US); Xiaobo Wang, San Diego, AZ (US)

(73) Assignee: ACEA Biosciences, Inc., San Diego, CA (US)

(*) Notice: Subject to any disclaimer, the term of this patent is extended or adjusted under 35 U.S.C. 154(b) by 0 days.

(21) Appl. No.: 13/309,209

(22) Filed: Dec. 1, 2011

(65) Prior Publication Data

US 2013/0143254 A1 Jun. 6, 2013

(51) Int. Cl.
| | | |
|---|---|---|
| C12M 1/12 | (2006.01) |
| C12Q 1/02 | (2006.01) |
| G01N 33/543 | (2006.01) |
| G01N 21/25 | (2006.01) |
| G01N 21/64 | (2006.01) |
| G01N 33/487 | (2006.01) |

(52) U.S. Cl.
CPC ............. *C12M 25/04* (2013.01); *C12Q 1/02* (2013.01); *G01N 33/54373* (2013.01); *G01N 21/253* (2013.01); *G01N 21/6452* (2013.01); *G01N 33/48735* (2013.01)

(58) Field of Classification Search
CPC ....... C12M 25/04; C12Q 1/02; G01N 21/253; G01N 21/6452; G01N 27/02; G01N 27/041; G01N 33/54373
USPC ........................................ 435/283.1–309.4
See application file for complete search history.

(56) References Cited

U.S. PATENT DOCUMENTS

| | | | |
|---|---|---|---|
| 4,871,674 A | 10/1989 | Matsui et al. |
| 5,026,649 A | 6/1991 | Lyman et al. |
| 5,534,227 A | 7/1996 | Lahm et al. |
| 5,652,142 A | 7/1997 | Barker et al. |
| 5,665,596 A | 9/1997 | Mussi |
| 5,801,055 A * | 9/1998 | Henderson ............. 435/297.5 |
| 7,135,148 B2 | 11/2006 | DeSilets et al. |
| 2003/0215940 A1* | 11/2003 | Lacey et al. ............ 435/305.2 |
| 2006/0121446 A1* | 6/2006 | Abassi et al. .................. 435/4 |

* cited by examiner

*Primary Examiner* — Nathan Bowers
*Assistant Examiner* — Lydia Edwards
(74) *Attorney, Agent, or Firm* — Wagenknecht IP Law Group PC

(57) ABSTRACT

An insert device and co-culture device assembly incorporating the insert device, which includes an insert chamber with two fluid impermeable side walls that extend from a microporous bottom to an open top to form an inner cavity. The first side wall is shaped to form a convex arc that follows between about half of a circumference of the well and less than an entire circumference of the well. The second side wall joins ends of the first side wall and protrudes inward towards a center of the convex arc. A flange extends outward from or beneath the top and is notched to form a gap adjacent to the second side wall, which forms an access port allowing access to the lower chamber with a micropipette tip when the insert device is inserted into a well of a single or multi-well plate.

18 Claims, 25 Drawing Sheets

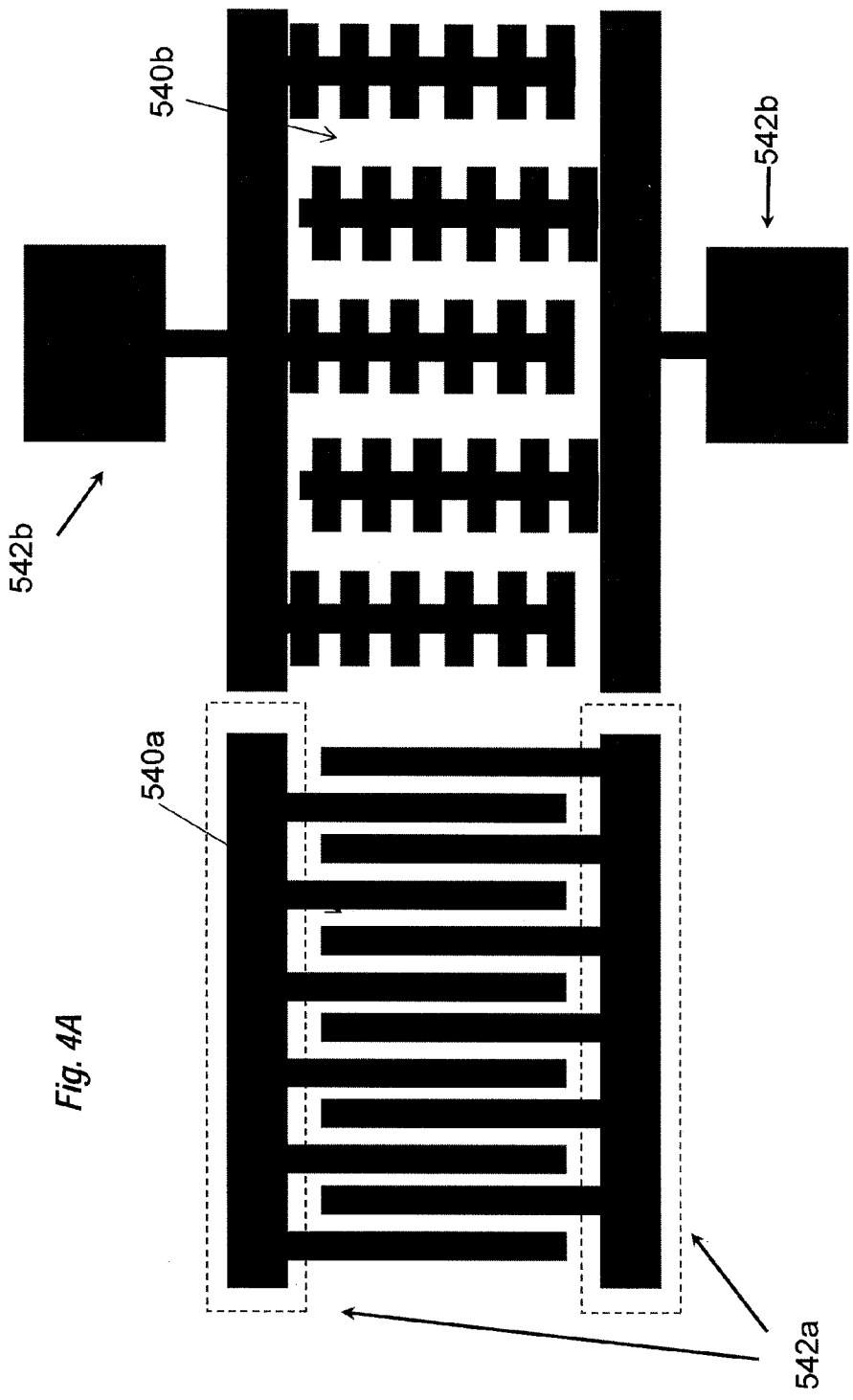

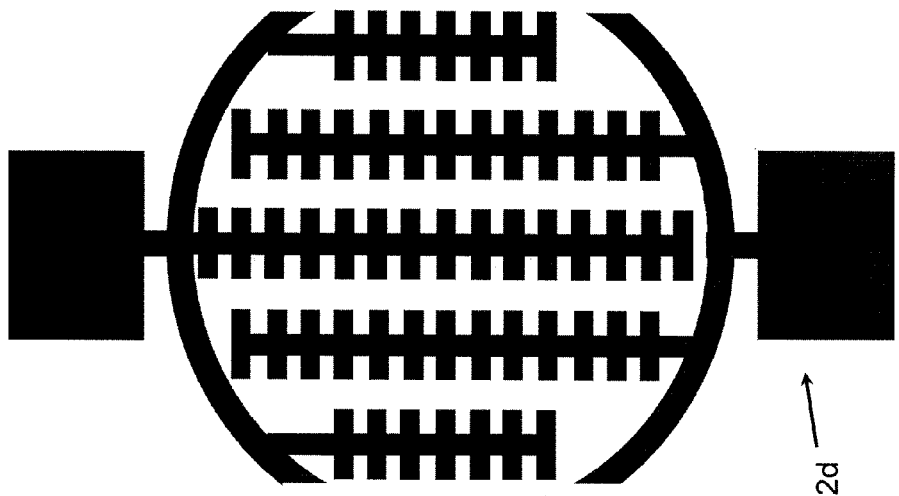
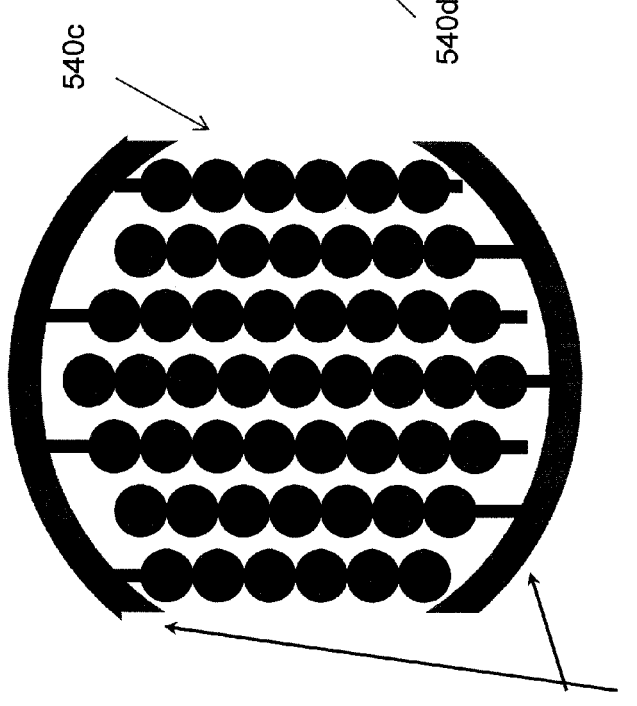
Fig. 4D
Fig. 4C

CO-CULTURE DEVICE ASSEMBLY

BACKGROUND OF THE INVENTION

1. Field of the Invention

This invention relates to devices and methods for the co-culturing of cells and more specifically to an insert device or tray that when assembled with a well or multi-well plate forms a co-culture device assembly having upper and lower chambers separated by a microporous membrane or barrier and method of use for the growing and/or assaying of biological cells.

2. Description of the Related Art

Various inserts having a porous bottom membrane for use with microtiter plates have been developed and are in use throughout the biological science community as dual chamber cell culture systems. Such systems are commonly used to culture or grow two types of cells in an indirect co-culture environment with one cell type growing in an upper chamber and another in a lower chamber. One such use is to assess the potential relationship between "effector" cells and "target" cells. Specifically, effector cells may secrete molecules which may act on target cells, causing different biological effects such as, promoting the growth of target cells, causing cytotoxic effects on target cells, or activating specific receptors or other molecular targets on the target cells. Thus, the combination of the insert and the microtiter plate is useful to examine the indirect interactions between two different cell lines or cell types, such as paracrine signaling affecting cell proliferation, cell survival and cytotoxicity effect. This paracrine signaling effect can be assayed by readouts such as end-point assay readouts (e.g. MTT based assays using plate reader and imaging based readout) in regular micro-titer plates. Examples of such devices have been described in a number of US patents, including U.S. Pat. No. 5,026,649; U.S. Pat. No. 4,871,674; U.S. Pat. No. 5,366,893; U.S. Pat. No. 5,534,227; U.S. Pat. No. 5,801,055; U.S. Pat. No. 5,665,596; U.S. Pat. No. 5,583,037. Current approaches typically suffer from one or more challenges. Among these include challenges associated with movement of the insert within the multi-well plate when accessing the lower chamber, potential contamination from the upper chamber when accessing the lower chamber and the addition of complex features or mechanisms to reduce movement of the upper chamber. Further, some configurations are labor intensive and reveal only limited information at a single time point. Accordingly, there remains a need to develop new devices, systems and methods that reduce chamber movement, reduce potential sample contamination, are simple to operate and offer a variety of information across multiple time points.

SUMMARY OF THE INVENTION

The invention addresses the above needs and provides related benefits. In one aspect, the invention is directed to an insert device that can be used in combination with a single or multi-well plate to form an upper chamber and lower chamber system for co-culturing two types of cells, where one type of the cells is cultured in the upper chamber and another type in the lower chamber. In particular, the insert device includes an insert chamber with two fluid impermeable side walls that extend from a microporous bottom to an open top to form an inner cavity. The first side wall is shaped to form a convex arc that follows between about half of a circumference of the well and less than an entire circumference of the well. The second side wall joins ends of the first side wall and protrudes inward towards a center of the convex arc. A flange extends outward from or beneath the top and partially surrounds the perimeter of the insert chamber, which together with the side wall configuration serves to position the insert device in relation to wells of a well plate. The flange is notched to form a gap adjacent to the second side wall, which forms an access port allowing access to the lower chamber with a micropipette tip when the insert device is inserted into a well of a single or multi-well plate.

In some embodiments the insert chamber includes an outer ridge vertically above the flange and encircling the open top of the insert chamber serving to inhibit liquid contamination between neighboring chambers when the insert device is used in a multi-well plate. Contamination may also be discouraged/minimized by positioning a recess along the underside of the flange that disrupts the underside surface of the flange thereby preventing or reducing potential liquid transfer across the flange. The insertion chamber can be characterized as having a generally kidney-shaped cylindrical configuration or having two side walls that are each characterized as having a convex configuration that bulge in a same direction. In some embodiments the first wall follows about two thirds of the circumference of the well. In a related aspect the invention also provides an insert tray including a plurality of insert chambers joined by a common flange for insertion into wells of a multi-well plate. Each chamber includes two fluid impermeable side walls extending from a microporous bottom to an open top to form an inner cavity. The first side wall is shaped to form a convex arc that follows between about half of a circumference of the well and less than an entire circumference of the well. The second side wall joins ends of the first side wall and protrudes inward towards a center of the convex arc. The common flange extends outward from or beneath each top and partially surrounds the perimeter of each insert chamber. The flange is notched to form a gap adjacent to each second side wall. In some embodiments the gap is a common gap shared by at least two insert chambers.

In yet another aspect of the invention a co-culture device assembly is provided. In a first embodiment the co-culture device assembly includes the insert device and a well or a multi-well plate. When the insert device is inserted into the well the flange suspends the microporous bottom above a bottom of the well to form an upper chamber defined by the inner cavity of the insert chamber and a lower chamber. The lower chamber is accessible through an access port formed by the gap and a well side wall. In a second embodiment the co-culture device assembly includes the insert tray and a multi-well plate. In this embodiment, the common flange suspends each microporous bottom above each corresponding bottom of the well to form a plurality of upper chambers defined by the inner cavities of the insert chambers and a plurality of lower chambers. The lower chambers are accessible through access ports formed by gaps and side wall of the wells.

Providing the well or multi-well plate together with the insert device or insert tray can provide additional benefits over offering the insert device or insert tray separately. Among these include complete co-culture device assemblies that incorporate advanced cell detection or cell monitoring capabilities. In some embodiments, the well or multi-well plate includes electrodes for monitoring changes in cell culture characteristics, such as changes in impedance, resistance, reactance and the like that may be attributed to cell toxicity, cell proliferation, morphological changes and the like. Impedance monitoring of cells can be achieved by detecting or measuring changes of a cell population cultured on the electrodes in the lower chamber. In other embodiments the well or multi-well plate is provided to facilitate optical detection or imaging methodologies, such as those that measure changes in optical properties or producing a cell culture image. In still other embodiments, the co-culture device assembly permits both electrical measurement and optical measurement to provide combined capabilities.

In yet another aspect of the invention, a system for monitoring cells under a co-culture condition is provided. The system includes an insert tray; a multi-well plate; and a means for measuring a cell culture characteristic. In one embodiment, the multi-well plate has electrodes incorporated into the chamber wells, and an impedance analyzer capable of measuring electrical impedances of the electrodes in the multi-well plate. Such a system may also include a device station for convenient connectivity between one or more multi-well plates, an impedance analyzer and may include a computer loaded with suitable programming to instruct initiation or continuation of impedance measurements, storing measurements, data analysis and the like.

In yet another aspect of the invention a methods of culturing and monitoring cells using devices of the present invention are provided. An exemplary method includes the following steps: providing the system or co-culture device assembly of the present invention, which includes a multi-well plate and an insert tray including multiple insert chambers, adding one type of cell to wells of the multi-well plate, adding another type of cells into the insert chambers of the insert tray, assembling the insert tray with the multi-well plate to form upper and lower chambers, and monitoring the cells cultured in the device. In one embodiment, monitoring cells includes imaging cells cultured in wells of the multi-well plate at different time points of cell culture. In another embodiment, monitoring cells includes performing WST or MTT assays to monitor viable cell numbers in wells of the multi-well plate at the end of an assay. In another embodiment, wells of the multi-well plate include microelectrode arrays used for monitoring cells grown on electrodes and monitoring cells includes measuring electrode impedances when the cells are cultured in the multi-wells at single or multiple time points. In some embodiments a compound is added to a chamber to determine its effect on the cell co-culture. Such compounds may be stimulants, inhibitors and the like.

BRIEF DESCRIPTION OF THE DRAWINGS

FIGS. 4A-F are schematic representations of electrode geometries that can be used in the devices for assaying and monitoring cells. In FIG. 4A, an interdigitated 540a, parallel line electrode array is shown, where the electrode width can be larger, equal to, or smaller than the electrode gaps. In FIG. 4B a castellated and offset electrode structures 540b are shown. In FIG. 4C a circle on line 540c or disc on line electrode geometry is shown. In FIG. 4D castellated, straight electrode structures 540d are shown. In FIG. 4E sinusoidal electrode structures 540e are shown. In FIG. 4F concentric electrode structures 540f are shown. The characteristic dimension of the electrodes can be as small as less than 10 microns, or as large as over several hundred microns. The total active electrode area can be of different shapes such as regular shapes like rectangular shapes (FIGS. 4A, 4B, 4E), or circle-like shapes (FIGS. 4C, 4D), or other regular or irregular shapes. Preferably, the total electrode-region area (the area including the electrodes and the gaps between the electrodes) covers nearly the complete bottom surface of the wells of multi-well plates. Electrode structures are connected to impedance measurement circuits (e.g. an impedance analyzer) via connection pads (as illustrated in FIGS. 4A and 4B) that are either directly linked to electrode elements (FIG. 4A, FIG. 4C and FIG. 4E) or connected to electrode elements through additional electrical connection (FIG. 4B and FIG. 4D). In FIGS. 4A, C and E, connection pads are also the electrically-conducting connection traces that connect electrode elements within an electrode structure.

(FIGS. 11B, 11C) The Cell Index increases mediated by U87 is through VEGF signaling pathway, as the Cell Index responses can be blocked by a neutralizing mAb against VEGF (FIG. 11C), but not by a control IgG (FIG. 11B).

DETAILED DESCRIPTION

Figure 1A:
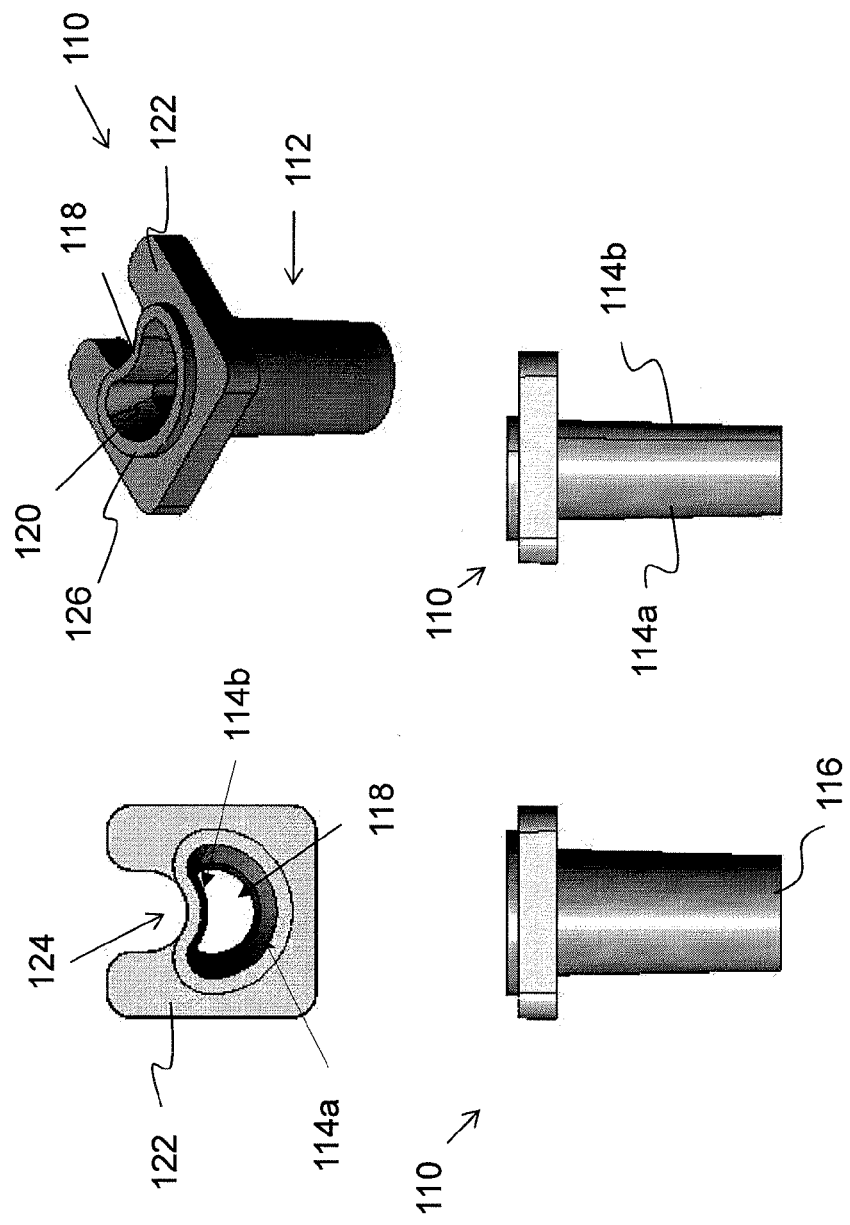
FIG. 1A is a schematic representation showing a top plan view, front elevational view, side elevational view and an isometric view of an insert device 110.

For clarity of disclosure, and not by way of limitation, the detailed description of the invention is divided into an introduction and subsections that follow.

The present invention provides devices, systems and methods for cell-based assays. Among the benefits of the invention are improvements for accessing, treating and measuring spatially distinct populations of cells that can be effected by or communicate with other spatially distinct populations of cells. That is, while cell populations are permitted to interact or communicate through a fluid medium, their physical separation permits monitoring of each population separately. Further, by providing improved chamber and flange configurations it is easier for the user to selectively access each chamber while conducting cell based assays thereby preventing disruption of the other chamber.

Cell-based assays are further improved through the use of impedance sensing technology, which provides a non-invasive measurement so that the cells can be monitored in real-time and continuously. Yet the cells can still be used for other cell-based or molecular-based assays after the impedance-based sensing. In comparison to traditional cell-based assays, the impedance-based sensing system provides additional benefits including improved kinetic information as for the cell number and cell biological status (including their attachment status, morphology, viability, receptor activation etc.) under a co-culture condition where one cell type serves as stimulating cells or effector cells and another cell type serves as target cells for monitoring. In addition, the measurement process can be label-reagent free, thus saving the cost for labeling reagents and labor efforts involved in manufacturing, handling and adding labeling reagents. Furthermore, the entire measurement process can be computer-controlled and fully automated. In such configurations the user need only to seed cells for the co-culture assay, and, optionally, to add appropriate compounds (for example, stimulation molecules to stimulate/activate/affect the effector in the insert chamber (or assembled upper chamber) or target cells in the wells (or assembled lower chambers), for the required assay process. Finally, the measurement system is accurate with high reproducibility and repeatability. It is also be very sensitive, expressed in the number of the cells per unit area (e.g., about 5 cells/mm$^2$).

A. DEFINITIONS

For clarity of disclosure, and not by way of limitation, the detailed description of the invention is divided into the subsections that follow.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "microporous" refers to a porosity that prevents passage of eukaryotic cells. A "microporous bottom" prevents passage of eukaryotic cells through a bottom of the insert chamber but permits passage of fluids and analytes in aqueous solution. A "microporous membrane" is a membrane that prevents passage of eukaryotic cells but permits passage of analytes in aqueous solution.

As used herein, "membrane" is a sheet of material.

As used herein, "biocompatible bottom" or "biocompatible membrane" means a bottom or membrane that does not have deleterious effects on cells, including the viability, attachment, spreading, motility, growth, or cell division. Preferably, the biocompatible bottom or membrane has a surface that is suitable for cell attachment and/or growth. When a suspension of viable, unimpaired, epithelial or endothelial cells is added to a chamber or well, a surface of the chamber or well "is suitable for cell attachment" when a significant percentage of the cells are adhering to the surface of the chamber or well within twelve hours. Preferably, at least 50% of the cells are adhering to the surface of the chamber or well within twelve hours. More preferably, a surface that is suitable for cell attachment has surface properties so that at least 70% of the cells are adhering to the surface within twelve hours of plating (i.e., adding cells to the chamber or well). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating. To have desired surface properties for cell attachment, the surface may need to be chemically-treated (e.g. treatment with an acid and/or with a base), and/or physically treated (e.g. treatment with plasma), and/or biochemically treated (e.g. coated with one or more molecules or biomolecules that promotes cell attachment). In the present invention, a biocompatible surface (such as a biocompatible bottom or membrane or well bottom) preferably is suitable for the attachment of cells of the type that are to be used in an assay that uses the biocompatible surface and most preferably, allows the attachment of at least 90% of the cells that contact the biocompatible surface during the assay.

As used herein, "follows the circumference of a well" or "follows a side wall of a well" refers to a shape that mimics or resembles the circular shape of the well. A well is typically circular and thus a shape that "follows a side wall of a well" is typically rounded or has a near rounded structure; however, the shape need not be perfectly round.

As used herein, "following the perimeter" refers to a shape that mimics or resembles the shape of a perimeter.

As used herein, "kidney-shaped" refers to an oval or circle with an inward curve at one side.

As used herein, "center of a convex arc" is the position downward from the top or apex of an arc by an amount equal to its radius.

As used herein, "bulge" refers to a protrusion.

As used herein, "biomolecular coating" is a coating on a surface that comprises a molecule that is a naturally occurring biomolecule or biochemical, or a biochemical derived from or based on one or more naturally occurring biomolecules or biochemicals. For example, a biomolecular coating can comprise an extracellular matrix component (e.g., fibronectin, collagens), or a derivative thereof, or can comprise a biochemical such as polylysine or polyornithine, which are polymeric molecules based on the naturally occurring biochemicals lysine and ornithine. Polymeric molecules based on naturally occurring biochemicals such as amino acids can use isomers or enantiomers of the naturally-occurring biochemicals.

As used herein, "electrode" is a structure having a high conductivity, that is, a conductivity much higher than surrounding material.

As used herein, an "electrode structure" refers to a single electrode, particularly one with a complex structure (as, for example, a spiral electrode structure), or a collection of at least two electrode elements that are electrically connected together. All the electrode elements within an "electrode structure" are electrically connected.

As used herein, "electrode element" refers to a single structural feature of an electrode structure, such as, for example, a fingerlike projection of an interdigitated electrode structure.

As used herein, an "electrode structure unit" is two or more electrode structures that are constructed to have dimensions and spacing such that they can, when connected to a signal source, operate as a unit to generate an electrical field in the region of spaces around the electrode structures. Preferred electrode structure units of the present invention can measure impedance changes due to cell attachment to an electrode surface. Non-limiting examples of electrode structure units are interdigitated electrode structure units and concentric electrode structure units.

As used herein, "electrode traces" are electrically conductive paths that extend from electrodes or electrode elements or electrode structures toward one end or boundary of a device or apparatus for connecting the electrodes or electrode elements or electrode structures to a signal source. The end or boundary of a device may correspond to the connection pads on the device or apparatus.

As used herein, "the at least two electrodes (electrode arrays) have substantially same surface area" means that the surface areas of any electrodes (electrode arrays) are not substantially different from each other so that the impedance change due to cell attachment or growth on the larger electrode (electrode array) will contribute to the overall detectable change in impedance to a same or similar degree as the impedance change due to cell attachment or growth on the smaller electrodes (electrode arrays). In other words, both larger electrodes (electrode arrays) and smaller electrode (electrode arrays) contribute to overall change in impedance upon cell attachment or growth on these electrodes. Ordinarily, the ratio of surface area between the largest electrode (electrode array) and the smallest electrode (electrode array) is less than 10. Preferably, the ratio of surface area between the largest electrode (electrode array) and the smallest electrode (electrode array) is less than 5, 4, 3, 2, 1.5, 1.2 or 1.1. More preferably, the two electrodes (electrode arrays) have nearly identical or identical surface area.

As used herein, "interdigitated" means having projections coming one direction that interlace with projections coming from a different direction in the manner of the fingers of folded hands (with the caveat that interdigitated electrode elements preferably do not contact one another).

As used herein, "the device has a surface suitable for cell attachment or growth" means that the electrode and/or non-electrode area of the well has appropriate physical, chemical or biological property so that desirable cells can viably attach on the surface and can keep attaching, while growing, on the surface. However, it is not necessary for the surface to contain any substances necessary for cell viability or growth. These necessary substances, e.g., nutrients or growth factors, can be supplied in a medium. Preferably, when a suspension of viable, unimpaired, epithelial or endothelial cells is added to the "surface suitable for cell attachment" when at least 50% of the cells are adhering to the surface within twelve hours. More preferably, a surface that is suitable for cell attachment has surface properties so that at least 70% of the cells are adhering to the surface within twelve hours of plating (i.e., adding cells to the chamber or well that comprises the said device). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating.

As used herein, "detectable change in impedance between or among the electrodes" means that the impedance between or among the electrodes would have a significant change that can be detected by an impedance analyzer or impedance measurement circuit when cells attach or grow on surfaces of the wells. The impedance change refers to the difference in impedance values when a surface of the well has cells attached or grown on and when a surface of the well does not have cells attached or grown on. Ordinarily, the change in impedance is larger than 0.1% to be detectable. Preferably, the detectable change in impedance is larger than 1%, 2%, 5%, 8%. More preferably, the detectable change in impedance is larger 10%. Impedance between or among electrodes is typically a function of the frequency of the applied electric field for measurement. "Detectable change in impedance between or among the electrodes" does not require the impedance change at all frequencies being detectable. "Detectable change in impedance between or among the electrodes" only requires a detectable change in impedance at any single frequency or multiple frequencies. In addition, impedance has two components, resistance and reactance (reactance can be divided into two categories, capacitive reactance and inductive reactance). "Detectable change in impedance between or among the electrodes" requires only that either one of resistance and reactance has a detectable change at any single frequency or multiple frequencies.

As used herein, a "high probability of contacting an electrode element" means that, if a cell is randomly positioned within the well, the probability of a cell contacting on an electrode element, calculated from the average diameter of a cell used on or in a device or apparatus of the present invention, the sizes of the electrode elements, and the size of the gaps between electrode elements, is greater than about 50%, more preferably greater than about 60%, yet more preferably greater than about 70%, and even more preferably greater than about 80%, greater than about 90%, or greater than about 95%.

As used herein, "dose-response curve" means the dependent relationship of response of cells on the dose concentration of a test compound. The response of cells can be measured by many different parameters. For example, a test compound is suspected to have cytotoxicity and cause cell death. Then the response of cells can be measured by percentage of non-viable (or viable) cells after the cells are treated by the test compound.

As used herein, "sample" refers to anything which may contain a moiety to be isolated, manipulated, measured, quantified, detected or analyzed using devices, microplates or methods in the present invention. The sample may be a biological sample, such as a cell, a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The biological samples also include cell suspensions, solutions containing biological molecules (e.g. proteins, enzymes, nucleic acids, carbohydrates, chemical molecules binding to biological molecules).

As used herein, a "liquid (fluid) sample" refers to a sample that naturally exists as a liquid or fluid, e.g., a biological fluid.

A "liquid sample" also refers to a sample that naturally exists in a non-liquid status, e.g., solid or gas, but is prepared as a liquid, fluid, solution or suspension containing the solid or gas sample material. For example, a liquid sample can encompass a liquid, fluid, solution or suspension containing a biological tissue.

B. CO-CULTURE DEVICE ASSEMBLIES AND DEVICES FOR USE IN CO-CULTURE DEVICE ASSEMBLIES OR ASSAYS

Single Chamber Insert Device and Assembly

Figure 1B:
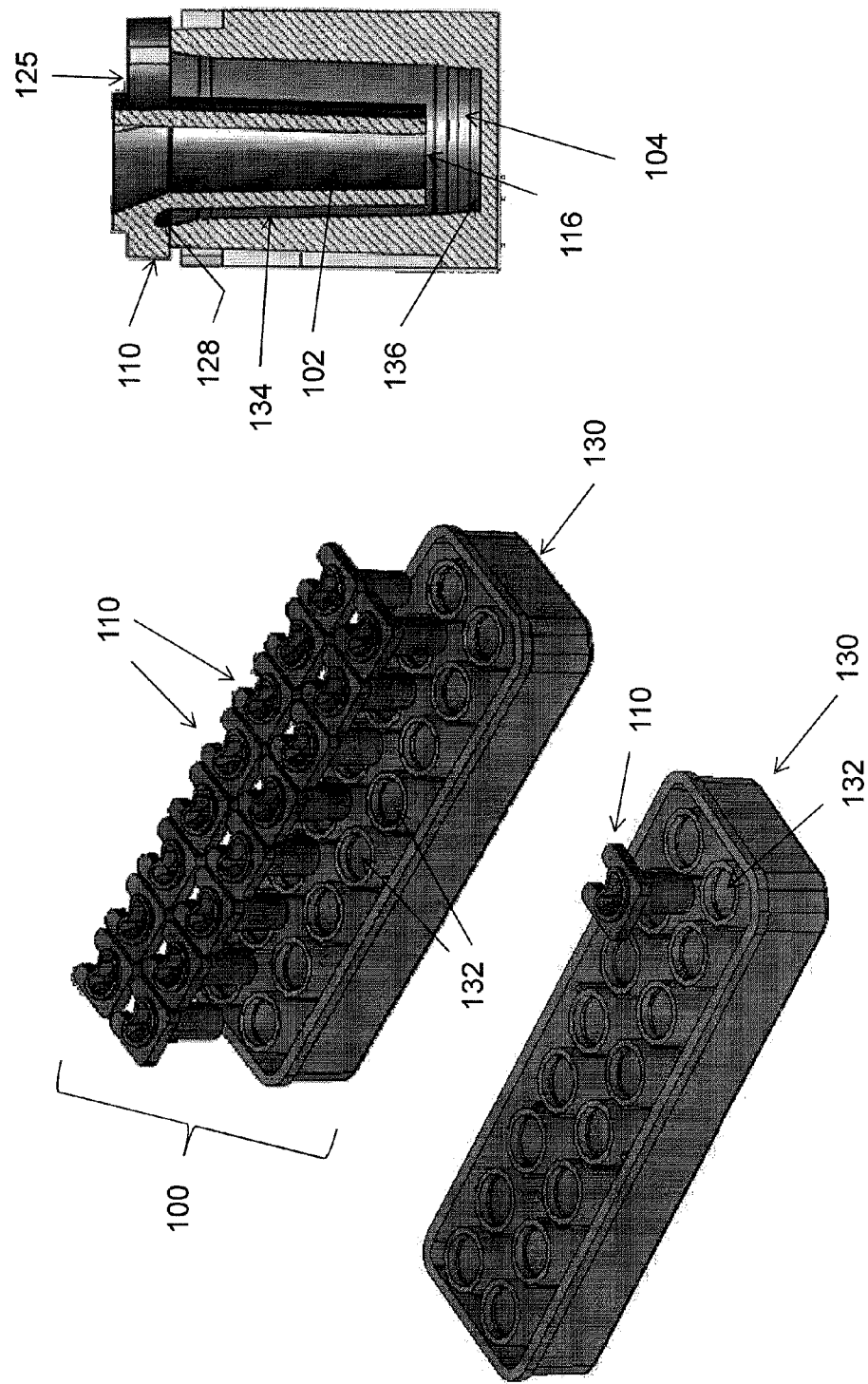
FIG. 1B is a schematic representation of a co-culture device assembly 100 in an exploded view including a single insert device 110 or multiple insert devices 110 for assembling with or insertion into a multi-well-plate 130 and a cross section of a single well 132 after insertion.
Figure 3A:
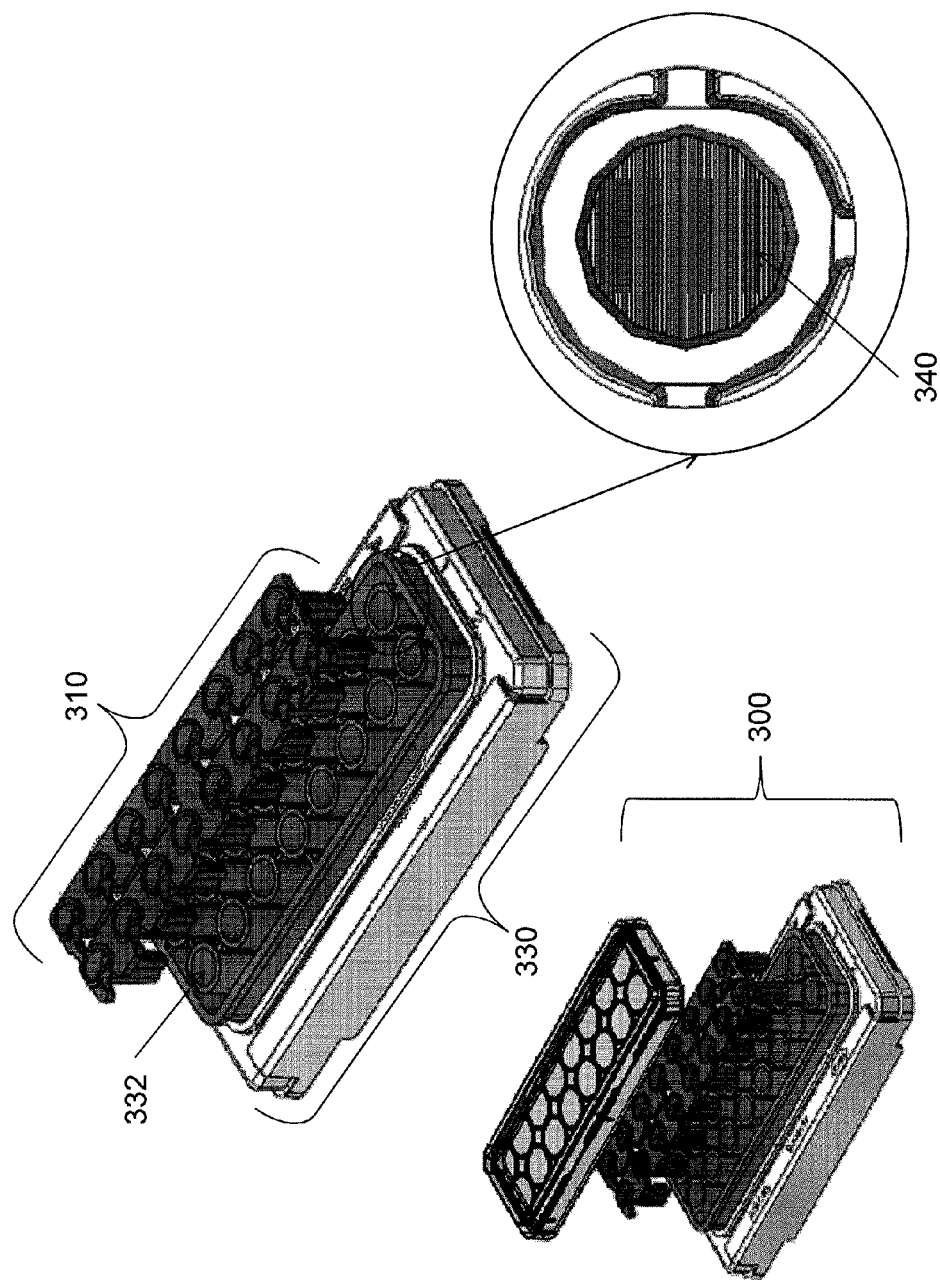
FIG. 3A is a schematic representation of a co-culture device assembly 300 for impedance monitoring in an exploded view and a partial cross section view, including an insert tray 310 for insertion into a multi-well plate 330, where the wells 332 of the multi-well plate 330 includes microelectrode structures 340. Here a 16-well chamber insert tray 310 and a 16-well plate 330 are shown.

Referring generally to FIGS. 1A and 1B, in one aspect of the invention, an insert device 110 is provided for insertion into a well 132, such as within a multi-well plate 130, to form a co-culture device assembly 100. The insert device 110 includes a chamber 112 for housing cells, which includes two fluid impermeable side walls 114a, 114b extending from a microporous bottom 116 to an open top 118 to form an inner cavity 120. A first side wall 114a is shaped to form a convex arc that follows between about half of a circumference of the well 132 and less than an entire circumference of the well 132. A second side wall 114b joins ends of the first side wall 114a and protrudes inwards towards a center of the convex arc. A flange 122 extends outward from or beneath the top 118 and partially surrounds the perimeter of the insert chamber 112. The flange 122 is notched to form a gap 124 adjacent to the second side wall 114b. The insert device 110 can be provided alone for use with a commercially available well 132 or multi-well plate 130 such as a variety of single well, six well, twelve well, sixteen well, twenty-four well, ninety six well plates and the like available from a variety of cell culture supply distributors to form the co-culture device assembly 100; however, in other embodiments, the insert device 110 is provided together with a well 132 or multi-well plate 130 as a complete co-culture device assembly 100. By providing the insert device 110 alone the user can form a desired device assembly 100 by selecting a desired well 132 or multi-well plate 130 that is capable of performing various measurements within the well. Referring briefly to FIG. 3A, in instances where specialized monitoring of a cell population is conducted, such as impedance monitoring, it may be preferable to provide a specialized multi-well plate 330, such as one that incorporates electrode structures 340 for impedance monitoring. Returning back to FIGS. 1A and B it may also be desirable to also provide a culturing multi-well plate 130 without electrodes to expand or grow cells in the insert device prior to an impedance monitoring experiment or the like.

Returning to the insert device 110, the side walls 114a, b are fluid impermeable, which means they are formed from a material that prevents passage of fluid. Examples of such materials include those used in the formation of tissue culture dishes, tubes, multi-well plates and the like. Among these include polystyrene, polycarbonate, polypropylene and the like. The side walls 114a, b are configured such that they extend from the microporous bottom 116 to the open top 118. In preferred embodiments both the microporous bottom 116 and open top 118 are each planar and parallel and thus in preferred embodiments the sidewalls 114a, b have a same or about a same height; however, they may be tapered the same or differently and thus may have different lengths. Since the side walls 114a, b extend to a same height selectively accessing the well 132 that forms a lower chamber 104 is performed outside of the insert chamber 112. This configuration reduces risk of contamination that may occur in technical approaches where the user traverses an upper chamber with a micropipette to selectively deliver a reagent to the lower chamber through a cutaway of the upper chamber side wall.

The joined first and second side walls 114a, b form a cylinder, which together with the microporous bottom 116, permits a biological sample, such as cells, to be added and cultured. In preferred embodiments the first side wall 114a is configured as a convex arc such that when inserted into a well 132, the first wall 114a follows the circumference of the side wall 134 of the well 132. By the term "convex arc" it is meant that the first side wall 114a has a curvature that bulges outward and thus after insertion into a well 132 coincides with the shape of the side wall 134 of the well 132. Most preferably, once inserted the convex arc has a same center as the side wall 134 of the well 132; however, a radius extending from the center to the convex arc is naturally smaller than a radius extending from the center to the side wall 134 of the well 134 to facilitate insertion. Further, the convex arc is preferably a smooth arc devoid of angles between its ends; however, the convex arc may also include a plurality of planar surfaces joined at angles that follow the curvature of the side wall 134 of the well 132. The skilled artisan will appreciate that a convex arc formed by increasingly smaller planar surfaces at increasing angles along the path of the side wall 134 of a well 132 will approach a smooth arc configuration. While the first side wall 114a preferably follows the well 130 at least halfway around its circumference or perimeter it should not follow the well 130 entirely around its circumference or perimeter thereby preventing the first side wall 114a from forming a complete circle. Most preferably the first side wall 114a follows about two thirds of the circumference of the well 132.

The ends of the first side wall 114a are joined by the second side wall 114b to form a cylindrical insert chamber 112, which together with the microporous bottom 106 is capable of housing cells. The second wall 114b is configured such that it protrudes inward towards the center of the convex arc. That is, the second side wall 114b does not continue along a same path as the first side wall 114a to form a cylinder having a continuous circular wall but instead, the cylinder is configured to include a depression inward towards its center. The formed depression results in a more a kidney-shaped cylinder rather than a circular cylinder. This preferred configuration can be formed by angling the mid-point of the second wall 114b inwards or preferably by shaping the second wall 114b in a convex configuration such that the bulge of the convex second side wall 114b protrudes inwards towards the center of the convex arc of the first side wall 114a. Put another way, the second side wall 114b can be shaped to form a convex arc that bulges in a same direction as the convex arc of the first side wall 114a. A convex arc of the first side wall 114a preferably has a longer radius than a convex arc of the second side wall 114b. Joining corners between the first side wall 114a and second side wall 114b are preferably rounded to further enhance cell culturing in the insert chamber 112.

Configuring the second side wall 114b such at it protrudes inward towards the center of the convex arc configuration of the first side wall 114a provides a number of benefits. Specifically, compared to circular chambers that are conventionally inserted into wells to form an upper chamber in a dual chamber system, in many instances the convex configuration permits the radius of the first wall 114a to be longer than the radius of a circular upper chamber for a same well. This increase in radius to the first side wall 114a of the insert chamber 212 can more closely approach the radius of the well 132 and thus reduce side to side and front to back motion of the upper chamber 102 within the lower chamber 104 in an assembled co-culture device assembly 100. Accordingly, cells are disrupted less and there is less risk of contamination.

While some technical approaches have developed additional protruding structures to further stabilize the positioning of the upper chamber, these further modifications are not needed in a convex arc configuration.

The flange 122 extends outward from or beneath the top 118 of the insert chamber 112 and thus at least partially surrounds the outer perimeter of the insert chamber 112. The flange 122 is shaped or configured such that it is not insertable into the well 132. Accordingly, as depicted in FIG. 1B, when the insert device 110 is inserted into the well 132 of a multi-well plate 130, the flange 122 suspends the microporous bottom 116 of the insert chamber 112 above the well bottom 136. The distance from the well bottom 136 to the microporous bottom 116 of the insert chamber 112 could be as low as 0.25 mm. In other embodiments, a large distance of 1 mm is preferred. Still, in other embodiments, even large distances from 1 mm to 3 mm may be preferred. In other embodiments, even larger distances above 3 mm may be preferred.

In addition, the flange 122 is notched to form a gap 124 adjacent to the second side wall 114b. By providing the gap 124 adjacent to the side wall 114b, the insert device 110 is structured in such a way that when the insert chamber 112 is inserted into the well 132 the gap 124 forms an access port 125 that permits selective access to the lower chamber 104 without disrupting the upper chamber 102.

Once the co-culture device 100 is assembled, preferably, the access port 125 is a cone-shaped port to selectively access the lower chamber 104 using a micropipette tip. This facilitates the selective addition of reagents, including colorimetric assay reagents, culture medium and the like to the lower chamber 104. Thus, the insert chamber 112 of the insert device 110, and in particular the second wall 114b, is formed in such a way as to create an adjacent clearance for liquid handling tools such as micropipette tips. This benefit is preferably achieved by incorporating the kidney-shaped geometry of the insert chamber 112 as shown in the top plan views of FIGS. 1A and 1B. In other words, while a convex arc configuration of the second side wall 114b permits the lengthening of the radius to the first side wall 114a, which reduces insert chamber 112 movement, its configuration also preferably provides sufficient clearance for a micropipette tip to access the lower chamber 104 without disrupting the upper chamber 102. Still further when positioning the gap 124 at about a center along a length of the flange 122, the gap 124 can be configured such that the access ports 125 across of a plurality of insert devices 110 can simultaneously receive a plurality of micropipette tips from a multi-channel micropipette thereby increasing throughput or consistency across multiple samples.

In one preferred embodiment of the insert device 110, to still further reduce a risk of contamination of liquids across neighboring insert chambers 112 or between insert chambers 112 and wells 132, the insert device 110 is equipped with two additional controlling features. The first is an outer ridge 126 encircling the open top 118 of the insert chamber 112. This ridge 126 helps to prevent liquids from passing directly from a first insert chamber 112 to an adjacent insert chamber 112 along neighboring flanges 122. The second controlling feature is located on the underside of the flange 122. Specifically, a recess 128 encircling each insert chamber 112 acts to inhibit liquid migration by creating a disruption in the bottom surface of the flange 122. In some embodiments the recess 128 is formed to accept the side wall 134 of a well 132.

The flange 122 can be formed integral with or within a same mold as the side walls 114a, b of the insert chamber 112. Preferably, each is made of a same plastic material, such as polystyrene, polyester (PET), polycarbonate (PC), or other suitable materials. In some embodiments the microporous bottom 116 is also formed simultaneously with the side walls 114a, b and flange 122; however, in many instances the microporous bottom 116 is formed separately then added after formation of the side walls 114a, b and flange 122. The skilled artisan will appreciate that a variety of methods can be used to form suitable plastic materials such as injection molding, precision machining, sintering or the like as known in the tissue or cell culture arts, cell-based assay arts and the like.

The passage of solutions, such as cell culture medium and analytes in aqueous solution, from the insert chamber 112 to the well 132 is regulated by the microporous bottom 126. Thus, the microporous bottom 126 provides a surface for culturing a cell population and defines the passage criteria from the upper chamber 102 to a lower chamber 104 in an assembled co-culture device assembly 100. The microporous bottom 116 can be formed from any suitable material. Non-limiting examples of the material include thin sheets of glass (e.g., quartz glass, lead glass or borosilicate glass), silicon, silicon dioxide on silicon, silicon-on-insulator (SOI) wafer, sapphire, plastics, and polymers. Some preferred polymers are polyimide (e.g. Kapton, polyimide film supplied by DuPont), polystyrene, polycarbonate, polyvinyl chloride, polyester, polyethylene terephthalate (PET), polypropylene and urea resin. Polymers such as polycarbonate, polyester and polyethylene terephthalate (PET) are especially preferred. The microporous bottom 116 may vary in thickness from as thin as about 2 microns, to as large as about 500 microns. Preferably, the microporous bottom 116 is between about 5 and about 50 microns thick, and more preferably between about 8 and about 25 microns thick.

The microporous bottom 116 may have any suitable surface areas. For example, the surface area may be between 30 and 50 mm$^2$, or between 10 and 30 mm$^2$, or between 3 and 10 mm$^2$, or between 1 and 3 mm$^2$, or between 0.3 and 1 mm$^2$. In another example, the surface area may be larger than 50 mm$^2$ but less than 100 mm$^2$. In still another example, the surface area may be larger than 100 mm$^2$. The surface area of the microporous bottom 116 is important as the cells are cultured on the membrane during the experiments using such insert devices 112. Thus, the choice of the microporous bottom 116 may be determined by desired number of the cells cultured in the insert chamber 112. For example, in a co-culture study where effector cells are cultured in the insert chamber 112, a small microporous bottom 116 area may limit the number of the effector cells, which in turn may limit amount of the molecules being released/produced/secreted from the effector cells, and thereby limit the potential response of target cells cultured in the wells 132. For such application, depending on the well volume and surface area of the wells 132 in the multi-well plate 130, the microporous bottom 116 may be, preferably, above 1 mm$^2$. Even more preferably, the microporous bottom 116 is between 3 and 10 mm$^2$. Still, more preferably, the microporous bottom 116 is between 10 and 30 mm$^2$. In other embodiments, the microporous bottom 116 area may be preferably between 30 and 50 mm$^2$.

The surface of the microporous bottom 116 exposed to cells during the use of an insert device 112 of the present invention is preferably biocompatible. Preferably, the surface of the bottom 116 facing into the insert chamber 112 or the inner cavity 120 is suitable for cell attachment or growth. Materials that are not biocompatible or do not allow optimum cell attachment or growth can be made suitable for cell attachment and growth by coating with another material, such as a polymer or biomolecular coating. Thus, the surface of a bottom 116 of the insert device 112 of the present invention can comprise a material, such as a plastic, that is suitable for cell attachment and growth, or, alternatively or in addition, can comprise a coating that allows cell to adhere to the bottom 116 surface.

The biocompatible bottom 116 can optionally comprise a coating that can promote the attachment of one or more cells. The coating can be a polymer, such as a plastic film or membrane, or one or more biomolecules or one or more derivatives of one or more biomolecules, such as, but not limited to a polymer such as polyornithine or polylysine, peptides or proteins, or extracellular matrix components (or derivatives or analogues thereof), including, but not limited to, gelatin, fibronectin, laminin, collagen, a glycosaminoglycan, a peptidoglycan, etc. Such coatings can preferably but optionally cover the entire surface of a bottom 116 that is exposed to or can be contacted by cells during the use of a device.

A coating can be a semi-solid or gel, and can optionally comprise additional components such as, but not limited to, growth factors. A coating can be a simple or complex mixture of biomolecules and can simulate or replicate a naturally occurring extracellular matrix (ECM.) For example, MATRIGEL Basement Membrane Matrix (BD BioSciences) is a solubilized basement membrane preparation extracted from the Engelbreth-Holm-Swarm (REHS) mouse sarcoma, a tumor rich in extracellular matrix proteins. Its major component is laminin, followed by collagen IV, heparan sulfate proteoglycans, entactin and nidogen. It also contains TGF-beta, fibroblast growth factor, tissue plasminogen activator, and other growth factors which occur naturally in the EHS tumor.

The microporous bottom 116 is porous and thus includes a plurality pores characterized as throughholes. The pores can be of any suitable size and shape combination that allows molecules and fluid to pass through the bottom 116 whilst preventing passage of eukaryotic cells from the inside of the insert chamber 112 to the well 132. The microporous bottom 116 can include multiple pores of a same size. Alternatively, the microporous bottom 116 can include multiple pores of different sizes. Further, some pores may be rounded while others may be slits. The pore sizes may be as small as less than 0.05 micron in diameter and as large as more than 1 micron in diameter. For example, the bottom 116 can comprise multiple pores of a same size that are between about 0.05 micron and about 3.0 microns in diameter, more preferably between about 0.1 microns and about 1.0 microns in diameter. In one embodiment, the bottom 116 includes multiple pores of about 0.1 micron in diameter. In one embodiment, the bottom 116 includes multiple pores of about 0.4 micron in diameter. Pores may be formed using a variety of techniques or methods such as track etching in a suitable membrane. Alternatively membranes of sufficient porosity may be purchased separately from a variety of vendors.

In preferred methods of manufacturing the co-culture device assembly 100 a microporous bottom 116 is formed then mounted to the side walls 114a, b. Various methods or techniques could be used to bond the bottom 116 to the side walls 114a, b of insert chamber 112, including liquid adhesive based bonding, solvent bonding, heat-pressure-assisted bonding, ultrasonic welding, laser welding and the like.

In liquid adhesive based bonding, the liquid adhesive is applied to either the bottom surface of the side walls 114a, b, or to the bottom 116, or even to both materials prior to assembling, such that the liquid adhesive fills the interface between the side wall 114a, b face and the bottom 116. The adhesive may be one of various adhesive types including hot-melt which is applied as a hot liquid and solidifies as it cools, two-part epoxies which undergo a chemical reaction upon mixing, thermal-cure epoxies which require heat to cure, and light-cure adhesives which require exposure to light in predetermined wavelength ranges (typically visible light, ultraviolet light, or both) in order to cure. Importantly, the liquid adhesive used for liquid adhesive based bonding should be bio-compatible and not have deleterious effects on cells, including the viability, attachment, spreading, motility, growth, or cell division.

In solvent bonding, exposure of the side walls 114a, b and bottom 116 to the solvent causes a localized melting of one or preferably both components. During this process, the components are held together such that as the volatile solvent evaporates, the melted materials combine and solidify to form a melted joint. Importantly, the solvent residue left behind on the insert chamber 112 after solvent evaporation, if any, should be bio-compatible and do not have deleterious effects on cells, including the viability, attachment, spreading, motility, growth, or cell division.

Heat-pressure assisted bonding utilizes elevated temperature to locally melt one of both materials. By assembling the bottom 116 to the side walls 114a, b while in this state, the melted materials mix and upon cooling, polymerize into a solid bonded joint. By assembling the components and pressing together with a hot iron, this process may be localized to the desired bonding area and optimized through control of the iron temperature, applied pressure, and time. Importantly, the heat-pressure assisted bonding process does not have any adverse effect on either side walls 114a, b or the bottom 116 to result in that either side walls 114a, b or the bottom 116 becomes no longer bio-compatible and has deleterious effects on cells, including the viability, attachment, spreading, motility, growth, or cell division.

Ultrasonic bonding requires a fixture which clamps the microporous bottom 116 and the side walls 114a, b. Bonding is achieved as high-energy vibrations, usually applied in the ultrasonic frequency range, are applied to the clamping fixture. This causes localized heating at the interface of the parts, and causes melting of one or both materials. This process may optionally be enhanced by forming a sacrificial energy director at the bottom surface of the side walls 114a, b. As the vibrational energy is applied, this sacrificial feature melts and after removal of the vibrational energy cools to form a solid bonded joint. Importantly, the ultrasonic bonding process does not have any adverse effect on either side walls 114a, b or the bottom 114 to result in that either side walls 114a, b or the bottom 116 becomes no longer bio-compatible and has deleterious effects on cells, including the viability, attachment, spreading, motility, growth, or cell division.

In the laser welding process, the bottom 116 is held to the bottom surface of side walls 114a, b while the bonding area is exposed to a laser light with a power large enough to cause melting of one or both materials. A catalyst may optionally be applied to either the bottom 116 or the side walls 114a, b such that the catalyst, when activated by the laser light, causes melting of one or both materials. Also, a mask may be optionally employed to constrain the laser light to only the target bonding area. Importantly, the laser welding process does not have any adverse effect on either side walls 114a, b or the bottom 116 to result in that either side walls 114a, b or the bottom 116 becomes no longer bio-compatible and has deleterious effects on cells, including the viability, attachment, spreading, motility, growth, or cell division.

Multi-Chamber Insert Tray for Use in a Co-Culture Device Assembly

Two or more insert devices 110 may be joined together at neighboring flanges 122 to form a multi-chamber configuration. Joining insert devices 112 may assist the user in forming co-culture device assemblies for higher throughput or for custom configurations. Joining insert devices 110 may be performed by interlocking complementary surfaces, such as snaps, tongue and groove, or the like on neighboring flanges 122 to provide a desired number and array of insert chambers 112. Alternatively, flanges 122 may be joined by gluing.

Figure 2A:
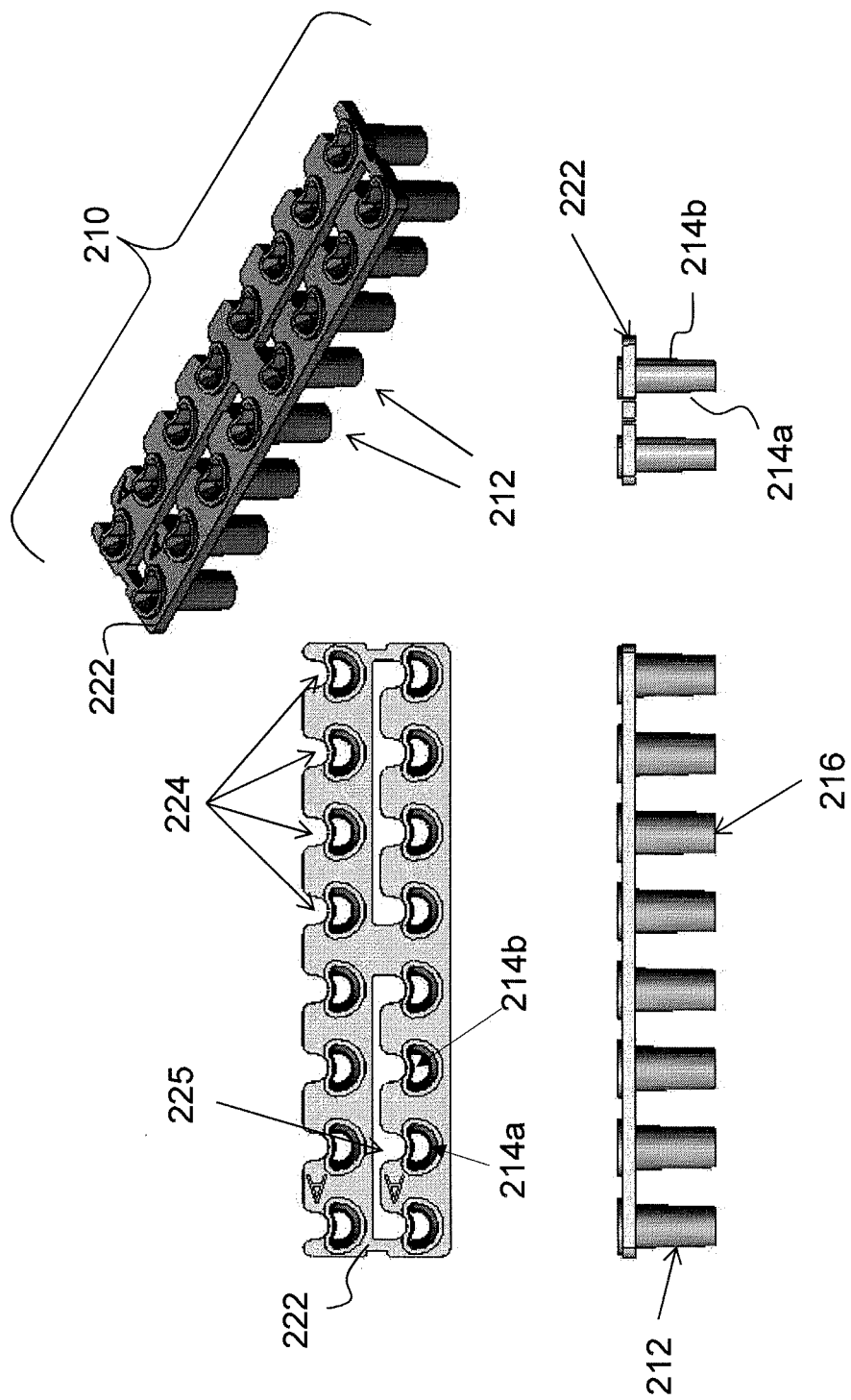
FIG. 2A is a schematic representation showing a top plan view, front elevational view, side elevational view and an isometric view of an insert tray 210 formed from a plurality of insert chambers 212 in an eight by two array and joined by a common flange 222.
Figure 2B:
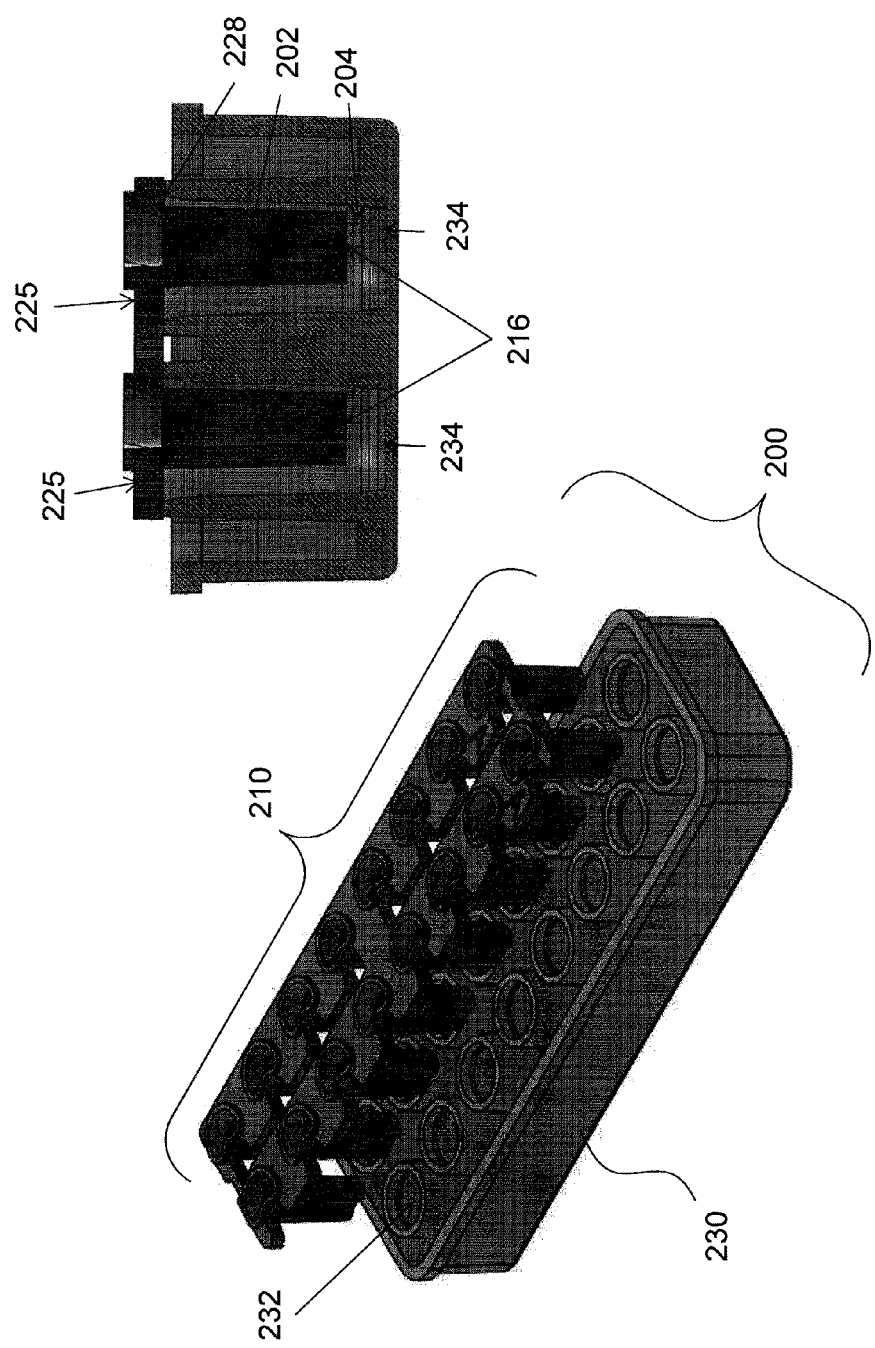
FIG. 2B is a schematic representation of a co-culture device assembly 200 in an exploded view including an insert tray 210 for assembling with or insertion into a multi-well plate 230 and a cross section of two neighboring wells 232 after insertion.

A preferred approach for a high throughput is to provide a multiple-chamber insert tray 210 as shown in FIGS. 2A and 2B that can be used in combination with a multi-well plate 230 to form a co-culture device assembly 200, which includes an upper chamber 202 and lower chamber 204 system for co-culturing two types of cells, where one cell type is cultured in the upper chambers 202 (i.e. insert chambers 212) and another type in the lower chambers 204 (i.e. wells 232 in the multi-well plate 230). Preferably, the multiple-chamber insert tray 210 includes a plurality of insert chambers 212 joined by a common flange 122. Each insert chamber 212 preferably includes two fluid impermeable side walls 214a, b extending from a microporous bottom 216 to an open top to form an inner cavity. A first side wall 214a is shaped to form a convex arc that follows between about half of a circumference of the well 232 and less than an entire circumference of the well 232. The second side wall 214b joins ends of the first side wall 214a and protrudes inwards towards a center of the convex arc. The common flange 222 extends outward from or beneath each top and partially surrounds the perimeter of each insert chamber 212. The common flange 222 is notched or bored to provide a gap 224 adjacent to each of the second side walls 214b. Preferably, the insert tray 210 further comprises a ridge encircling the top opening of each insert chamber 212 serving to reduce potential liquid contamination between neighboring insert chambers 212. Preferably, the bottom of the common flange 222 includes a recess 228 for each insert chamber 212, which encircles the insert chamber 212 and acts to inhibit liquid migration by creating a disruption in the bottom surface of the common flange 222.

The common flange 222 interconnects and thus joins each of the insert chambers 212. As such, the insert chambers 212 can be arrayed in a number of configurations. For instance, insert chambers 212 can be arrayed as one or more rows of two chambers, four chambers, six chambers, eight chambers, twelve chambers or the like. When arraying insert chambers 212 into rows, gaps 224 of neighboring insert chambers may be combined to form a common gap 225.

The common flange 222 is shaped or configured to prevent its insertion into any of the wells 232. Accordingly, as depicted in FIG. 2B, when inserted into a corresponding multi-well plate 230, the common flange 222 serves to set the height of each microporous bottom 216 in relation to the well 232 of the multi-well plate 230. The distance from the well bottom 234 to the microporous bottom 216 of the insert chamber 212 could be as low as 0.25 mm. In other embodiments, a large distance of 1 mm is preferred. Still, in other embodiments, even large distances from 1 mm to 3 mm may be preferred. In other embodiments, even larger distances above 3 mm may be preferred.

The common flange 222 is notched to form a gap 224 adjacent to each second side wall 214b of each insert chamber 212. By providing the gap 214 adjacent to the side wall 214b, the insert tray 210 is structured in such a way that when the insert chamber 212 is inserted into the well 232 the gap 224 forms an access port 225 that permits selective access to the lower chamber 204 without disrupting the upper chamber 202.

Preferably, the access port 225 is a cone-shaped port to further facilitate access to the lower chamber 204 using a micropipette tip. Thus, the insert chamber 212 of the insert tray 210, and in particular the second wall 214b, is formed in such a way as to create an adjacent clearance for liquid handling tools such as micropipette tips. This benefit can be achieved by incorporating the kidney-shaped geometry of the insert chamber 212 as shown in the top plan views in FIGS. 2A and 2B.

The insert tray 210 can be provided alone for use with commercially available multi-well plates 230, such as a variety of six well, twelve well, twenty-four well, or ninety six well plates and the like. In other embodiments, the insert tray 210 is provided together with a multi-well plate 230 as a co-culture device assembly 200. The multiple insert chambers 212 of the insert tray 210 are constructed such that when the insert tray 210 is assembled with the multi-well plate 232, the insert chambers 212 align with and fit into the wells 232 of the multiple well plate 230. Each insert chamber 212 preferably fits into a well 232 of the multi-well plate 230 such that the wells 232 of the multi-well plate 230 form lower chambers 204 and the insert chambers 212 of the insert tray 210 form upper chambers 202 for the co-culture device assembly 200 and the gaps 224 between the insert chambers 212 and the walls 232 of the multi-well plate 132 form a cone-shaped ports 225, allowing the access to the lower chambers 204 with micropipette tips without disrupting the upper chambers 202. In one embodiment, the insert tray 210 further includes a ridge encircling the top opening of the chamber(s) 212 serving to inhibit liquid contamination between neighboring chambers 212. In another embodiment, each well 232 of the multi-well plate 230 includes microelectrode structures for monitoring the impedance of cells cultured on the electrodes.

The materials for producing the insert tray 210, the biocompatible, microporous bottom 216, biocompatible coatings, methods used for producing insert trays 210 and the like are same as or similar to those in regards to the insert device 110 configuration discussed in detail.

C. SYSTEMS FOR MONITORING A CELL CULTURE

The co-culture device assembly can be further adapted for use with systems for monitoring cell culture characteristics. That is, a co-culture device assembly can be provided in a system including further technical advances, such as those that monitor changes within upper or lower chambers indicative of changes in cell viability, cell proliferation or the like. In some embodiments a system for monitoring a cell culture includes a system for monitoring an optical property of a cell population or culture. This can be accomplished by providing the co-culture device assembly together with a means for optical detection. In some embodiments, a means for optical detection includes an imaging device for producing a cell culture image. Among these include a variety of cameras, and optionally a computer loaded with software, to capture images of cells and optionally count and report total number of cells, number of viable cells and the like.

In a related embodiment, the system can include an optical plate reader that can identify particular optical wavelengths, such as those used in fluorescence detection. Fluorescence detection may be desired when fluorescent markers are available to indentify changes in cell population characteristics, such as viability or cell number. Among these fluorescein (FITC), phycoerythrin (PE) and others are commonly used and thus may be of particular interest. In some embodiments, the user adds labeled antibodies against surface markers associated with cell proliferation to the bottom chamber of the co-culture device assembly through the access port, medium is exchanged to wash away unbound antibodies and fluorescence is measured using an optical plate reader. In another embodiment a colorimetric assay such as a MTT assay is performed to assess cell proliferation and changes in color detected. Other examples of colorimetric assays that can be used include XTT, MTS and WST. In other embodiments, an optical detection device detects or measures light scatter, such as raman scattering or the like.

Figure 5:
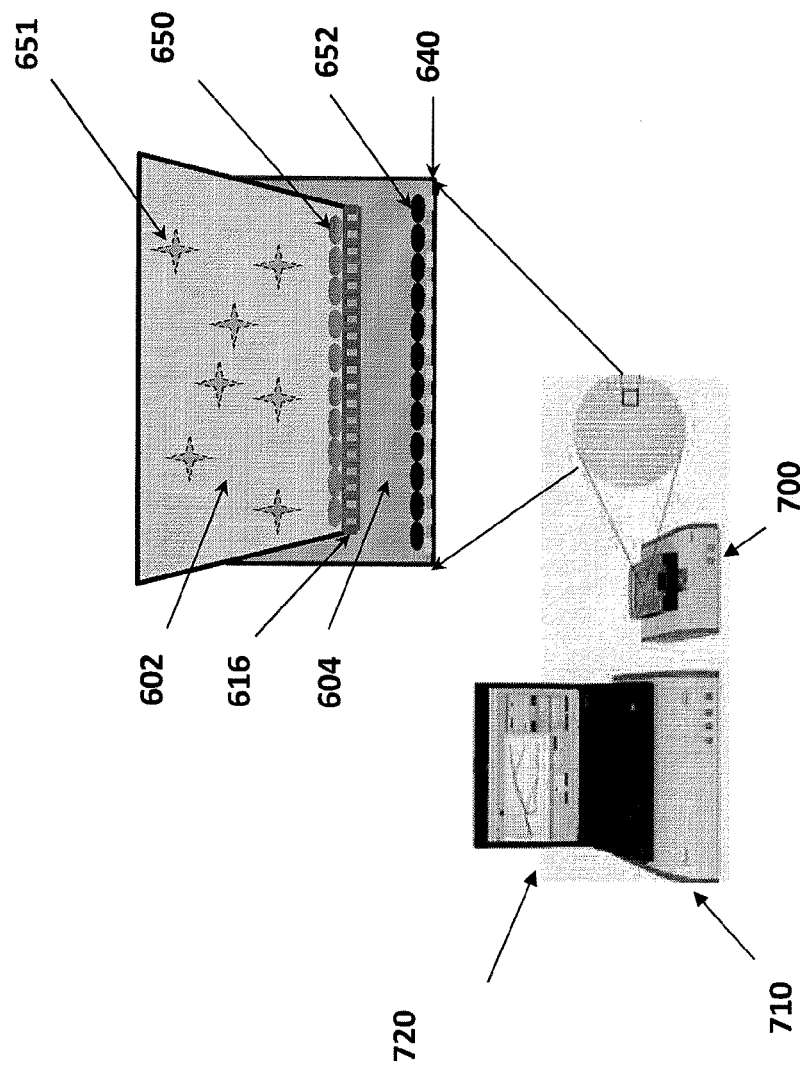
FIG. 5A is a schematic representation of a system actively monitoring a cell culture. An upper chamber 602 includes a microporous bottom 616 and a lower chamber 604 includes electrode structures 640. Effector cells 650 are cultured on the bottom 616 of upper chamber 602 and target cells 652 are cultured on the electrode surfaces 640 of the lower chamber 604. In the example shown in FIG. 5A, the target cells 652 cultured in the lower chamber 604 are monitored with an impedance sensing system (Roche Applied Sciences and ACEA Biosciences) including an impedance analyzer 710, an E-Plate station 700 which provides mechanical and electronic interfaces between E-Plates and the impedance analyzer, and a computer 720 with software that can communicate with and control the impedance analyzer 710 and E-Plate station 700. Molecules from the top chamber 602 secreted or produced by the effector cells 650 are permitted to pass through the pores on the microporous bottom 616 and reach the bottom chamber 604 to produce a biological effect on the target cells 652. In one option, stimulant molecules 651 are applied to the top chamber 602 to stimulate the effector cells 650 which may produce/release molecules upon stimulation. The released molecules from effector cells 650 are permitted to pass through the pores of the porous membrane 616 to reach the bottom chamber 604 thereby producing a biological effect on the target cells 652.
In FIG. 5B schematic representations of three types of co-culture effects: stimulation, toxicity and modulation, as monitored with impedance electrode sensing structures and shown with cell index as a readout. The broken lines show the time-dependent curves for the target cells cultured alone whilst the solid lines show those when the target cells are co-cultured with the effector cells in a co-culture setup. For such schematic representations, stimulation indicates that the target cells exhibit increased electrical impedance signals, toxicity indicates that the target cells exhibit decreased electrical impedance signals, modulation indicates that target cells exhibit "down-then-up" electrical impedance signals, under the influences of the effector cells.
Figure 5:
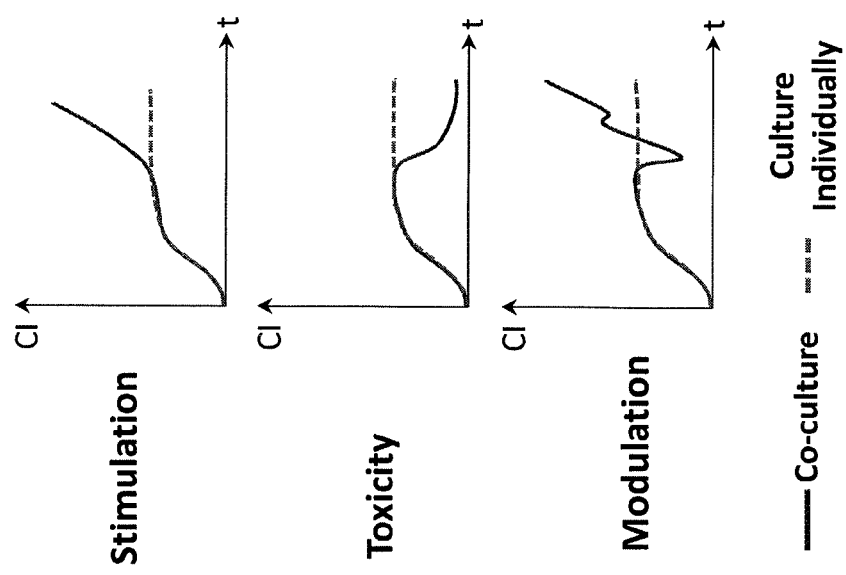

Turning to FIGS. 3A and B, in other embodiments the system for monitoring a cell culture includes monitoring impedance of a cell population. This can be accomplished by providing the insert device or insert tray 310, 410 together with a multi-well plate 330, 430 that includes suitable electrode structures 340, 440 on the bottom of the wells 332, 432 and as shown in FIG. 5A, providing an impedance analyzer 710, optionally coupled to a device station 700 and computer 720 loaded with software. Description of such multi-well plates 332, 432, including the composition of the multi-well plates 332, 432, the details of the electrode structure 340, 440, the methods of production and fabrication of such multi-well plates 332, 432 can be found in U.S. Pat. No. 7,459,303 B2 and U.S. Pat. No. 7,470,533, which are incorporated by reference in their entirety.

Multi-Well Plates with Incorporated Micro-Electrode Arrays at the Well Bottom

Returning to FIGS. 3A and B, in a preferred embodiment of the present invention, the multi-well plates 330, 430 used in the co-culture device assembly 300, 400 include microelectrode structures 340, 440 incorporated on a non-conductive substrate forming the well bottom. For each well 332, 432 of the multi-well plate 330, 430, the two electrode structures 340, 440 are fabricated on one side of such non-conductive substrate, facing into the wells 332, 432 of the multi-well plate 330, 430. Preferably the two electrode structures 340, 440 have substantially the same area. The two electrode structures 340, 440 having substantially the same area are preferably part of the same electrode structure unit for impedance monitoring of the cells cultured on the electrode structures.

The electrodes or electrode elements within an electrode structure in the present devices can have any suitable shape, e.g., a rectangular, circular, a circle on a rectangular line ("circle-on-line"), a square on a rectangular line or a sinusoidal line. They can also take the form of curved lines such as, but not limited to spirals or arcs. Some examples of electrodes, electrode structures or electrode structure units for the device of the present invention are shows in FIGS. 254A-F.

Figure 4E:
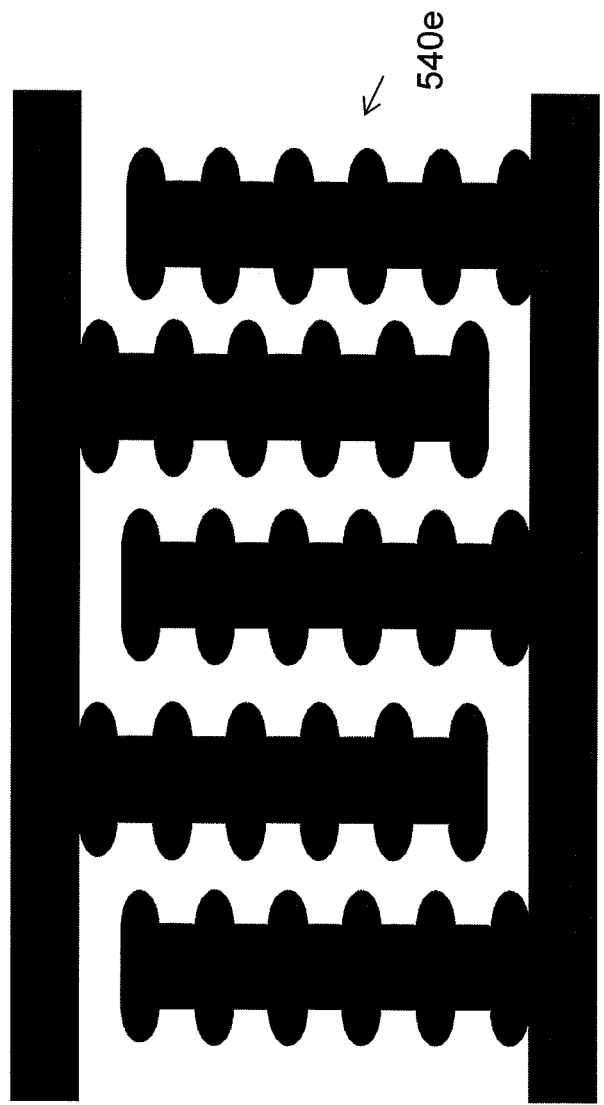
Figure 4E:
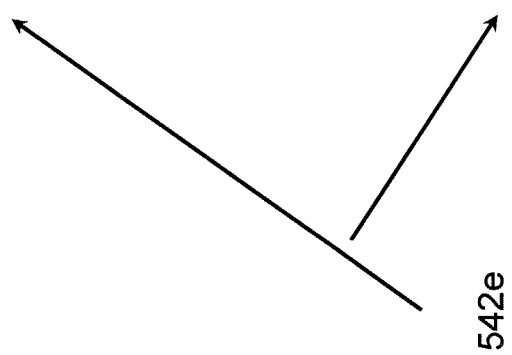
Figure 4F:
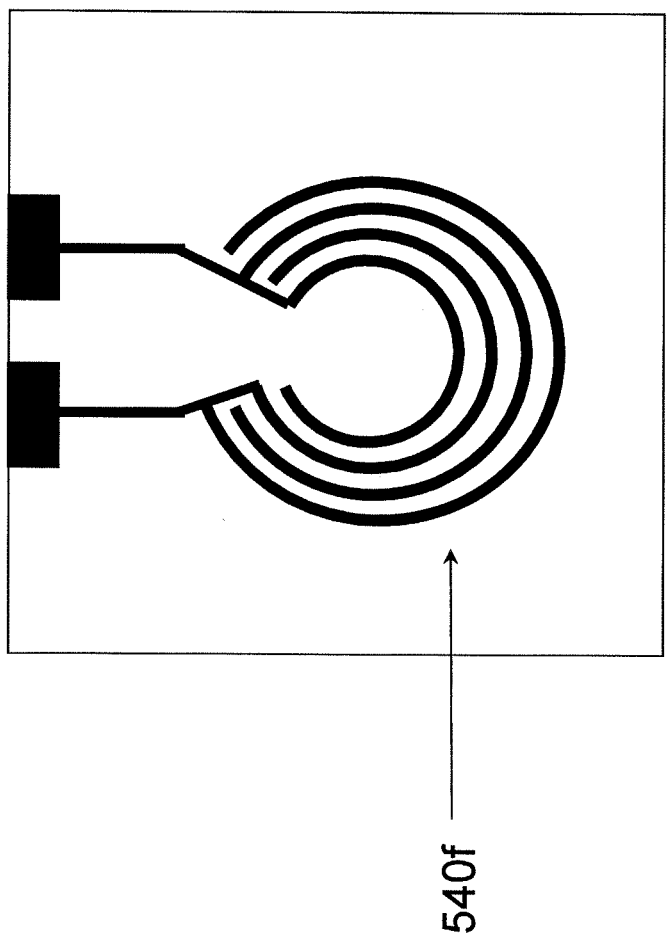

In some preferred embodiments of the present invention, electrode structures can be interdigitated electrode structures 540a (IDESs) or concentric electrode structures 540f (CCESs), such as those depicted in FIGS. 4A and 4F. For example, an electrode structure can comprise two or more electrodes configured as one or more IDESs or one or more CCESs. Interdigitated electrode structures (IDESs) can be further modified or changed so that the parallel line electrode elements have large perimeter subgeometries, meaning that, as viewed from above, superimposed on the linear electrode elements (which may itself be parallel lines, curved, loop, form angles, turn corners, etc.) are branches, outcroppings, bulges, and the like, giving the linear electrode path a larger perimeter than if its edges conformed to the directionality of the path of the electrode element. Examples of such large perimeter structures are a diamond-on-line electrode structures, circle-on-line electrode structures 540c shown in FIG. 4C, castellated electrode structures 540b, 540d as shown in FIGS. 4B and 4D. Electrode structures with large perimeter subgeometries are not limited to those depicted herein, and can be regular or irregular, both in the periodicity of the subgeometries and in the shapes of the subgeometries (curves, angles, circles, rectangles) themselves.

Electrodes or electrode elements are preferably distributed over the entire surface region of the well bottom they are fabricated on, wherein such surface region is or will be exposed to contact by cells. In another word, the surface region that is or will be exposed to contact by cells is covered with electrodes (or electrode elements) and gaps between electrodes (or electrode elements). In preferred devices of the present invention, the sensor area can occupy at least 5%, 10%, 30%, 50%, 70%, 80%, 90%, 95% or even 100% of the entire surface region of the device, wherein such surface region is exposed to or will be exposed to cells under the assay. In another word, in preferred devices of the present invention, at least 5%, 10%, 30%, 50%, 70%, 80%, 90%, 95% or even 100% of the surface region that is exposed or will be exposed to the cells under the assay is covered with electrodes (or electrode elements) and gaps between electrodes (or electrode elements). Preferably, the distribution of electrodes or electrode elements over the sensor area is uniform or approximately uniform.

Non-limiting examples of materials for electrodes or electrode elements are indium tin oxide (ITO), chromium, gold, copper, nickel, platinum, silver, steel, and aluminum. Electrodes can comprise more than one material. Choice of appropriate materials for making electrodes depends on several factors: whether the material is bio-compatible and is not cytotoxic, whether the material is conductive enough, how difficult it is for patterning such material on a substrate which forms the bottom surface of the wells of the multi-well plate.

Electrode or microelectrodes of the present invention can be of any electrically conductive material. For example, gold (Au), platinum (Pt) can be used. When substrates such as glass or plastics or polymer sheets are used to form the bottom surface of the wells of the multi-well plate, an adhesion layer of metal such as Cr and Ti can be used. In order to reduce the electric resistance of the electrodes, electrodes with conductive thin films are desirable to have certain thickness. As a non-limiting example, electrodes can be made with a Cr layer (for example, 10-300 Angstrom) overlaid by a thin gold film (for example, 500-1000 Angstrom). Such electrode layers will be optically non-transparent. Alternatively, optically-transparent electrodes can be used in a device of the present invention. Examples of optically transparent electrodes include indium-tin-oxide (ITO). With appropriate thickness of ITO layer, the transmittance of light through an ITO film electrode can be as high as 98%. In other cases, sufficiently thin conductive films (e.g. a very thin gold film) can be used as optically transparent electrodes. Choice of appropriate materials for making electrodes depends on several factors: whether the material is bio-compatible and is not cyto-toxic, the material is conductive enough, how difficult it is for patterning such material on a membrane substrate.

Various microfabrication methods can be employed for making such electrodes on a non-conductive substrate. One example is to use a photolithography technique. Those who are skilled in the art of photolithography fabrication and other microfabrication and micromachining methods can readily choose and use appropriate materials and specific procedures for fabricating microelectrodes. Another method of fabricating or patterning microelectrodes is to use laser ablation. Those who are skilled in laser ablation and thin film patterning with laser ablation can readily choose appropriate procedure and laser wave length, intensity, masks for producing electrodes on the polymer membranes.

The electrode elements, the electrodes, the electrode structures and the electrode structure units in the multi-well plates can have any suitable configurations, surface areas or surface modifications. In one example, at least one of the electrode structures can have at least two electrode elements. In still another example, the electrode or electrode structure surface area can be modified with a cell-adhesion promotion moiety. Any suitable cell-adhesion promotion moieties, such as a self-assembly-monomolecular (SAM) layer (e.g., alkanethiolates on gold and alkylsiloxanes on $SiO_2$ or SiOx), a protein (e.g., fibronectin, gelatin, collagen, laminin, proteins that promotes specific or non-specific cell attachment to the electrode or electrode array surface area), a peptide (e.g., poly-L-lysine), a polymer layer and a charged group, can be used in the present apparatuses.

Preferably, the electrodes, electrode structures, and electrode elements are configured such that the electrode traces lead from the electrodes at the substrate surface to a different area of the substrate (for example, a glass substrate or plastic sheet which forms the bottom surface of the wells in the multi-well plate), where they can be connected with a line from an impedance measurement circuit or a signal source. Here the area of the substrate where the electrode traces end may correspond to the connection pads on the substrate. In preferred aspects of the present invention, the trace or traces from electrode elements of one electrode structure are insulated from the traces from electrode elements of another electrode structure. In one type of arrangement, electrode traces are located on separate regions of the substrate such that they do not contact each other where their paths cross.

The multi-well plate of the present invention can have any suitable surface areas. For example, the well of the plate can have a bottom surface area sufficient for attachment of about 1-10, 10-100, 100-300, 300-700, 100-1000, 700-1,000, 1,000-3,000, 3,000-6,000, 6,000-10,000 or 1000-10000 cells. In another example, the bottom surface area of the well is between 30 and 50 $mm^2$, or between 10 and 30 $mm^2$, or between 3 and 10 $mm^2$, or between 1 and 3 $mm^2$, or between 0.3 and 1 $mm^2$.

The present multi-well plates can further comprise multiple connection pads to which one or more impedance analyzer can be connected. Electrodes or electrode structures can directly or indirectly connect to a connection pad, where they connect to a line from an impedance analyzer. A connection pad is preferably at the edge or perimeter of the multi-well plate of the present invention, but this is not a requirement of the present invention. The connection between electrodes and a connection pad can optionally be via a connecting path that can be localized to an end of the substrate. Various connecting pad configurations 542*a-e* are shown in FIGS. 4A-E.

The electrodes-containing substrates can be assembled onto a bottomless multi-well microtiter plates using various means, including but not limited to, bonding through pressure-sensitive-adhesives, liquid adhesives. Various techniques or methods of such assembly have been described previously in U.S. Pat. No. 7,459,303 B2 and U.S. Pat. No. 7,470,533, which are incorporated by reference in its entirety.

In yet another aspect, the present invention is directed to a system for monitoring cells under a co-culture condition. The system comprises a multi-chamber insert tray, a multi-well plate having electrodes incorporated into the chamber wells, an impedance analyzer capable of measuring electrical impedances of the electrodes in the multi-well plate.

Monitoring the Cells Cultured on Micro-Electrode Arrays at the Well Bottom

The cells cultured on microelectrodes in multi-well plate wells can be monitored using the system and methods described in U.S. Pat. No. 7,470,533 and U.S. Pat. No. 7,459, 303 B2, which are incorporated by reference in its entirety.

Such a system comprises a multi-well device incorporating microelectrode arrays at the well bottom, interface electronics, including impedance measurement circuit and switches (e.g. electronic switches), to control and switch the impedance measurement circuits to electrode structure units of multi-well plates. Preferably, such a system can also include a computer having software programs that can enable real-time measurement or monitoring of impedance between the electrodes or electrode structures of the multi-well plates. The measured impedance data can be automatically analyzed and processed to derive appropriate parameters (e.g. cell index, or cell number index) and displayed on a monitor. Preferably, the software program has one or more of the following functions: (1) electronically switching for connecting impedance measuring circuit (or analyzer) to one of multiple wells of the multi-well plate; (2) controlling impedance measurement circuit (or analyzer) for measurement of impedance between or among electrodes or electrode structures at one or multiple frequencies; (3) processing the acquired impedance data to derive appropriate biologically relevant parameters (e.g., cell index or cell number index); (4) displaying the results on a monitor or storing results; (5) automatically performing above functions 1 through 4 at regular or irregular time intervals.

Preferably, the impedance measurement circuits can measure or analyze impedance of the electrode structure units in any suitable frequency range, e.g., a frequency range between about 1 Hz and about 100 MHz, or between 10 Hz and about 5 MHz.

Figure 3B:
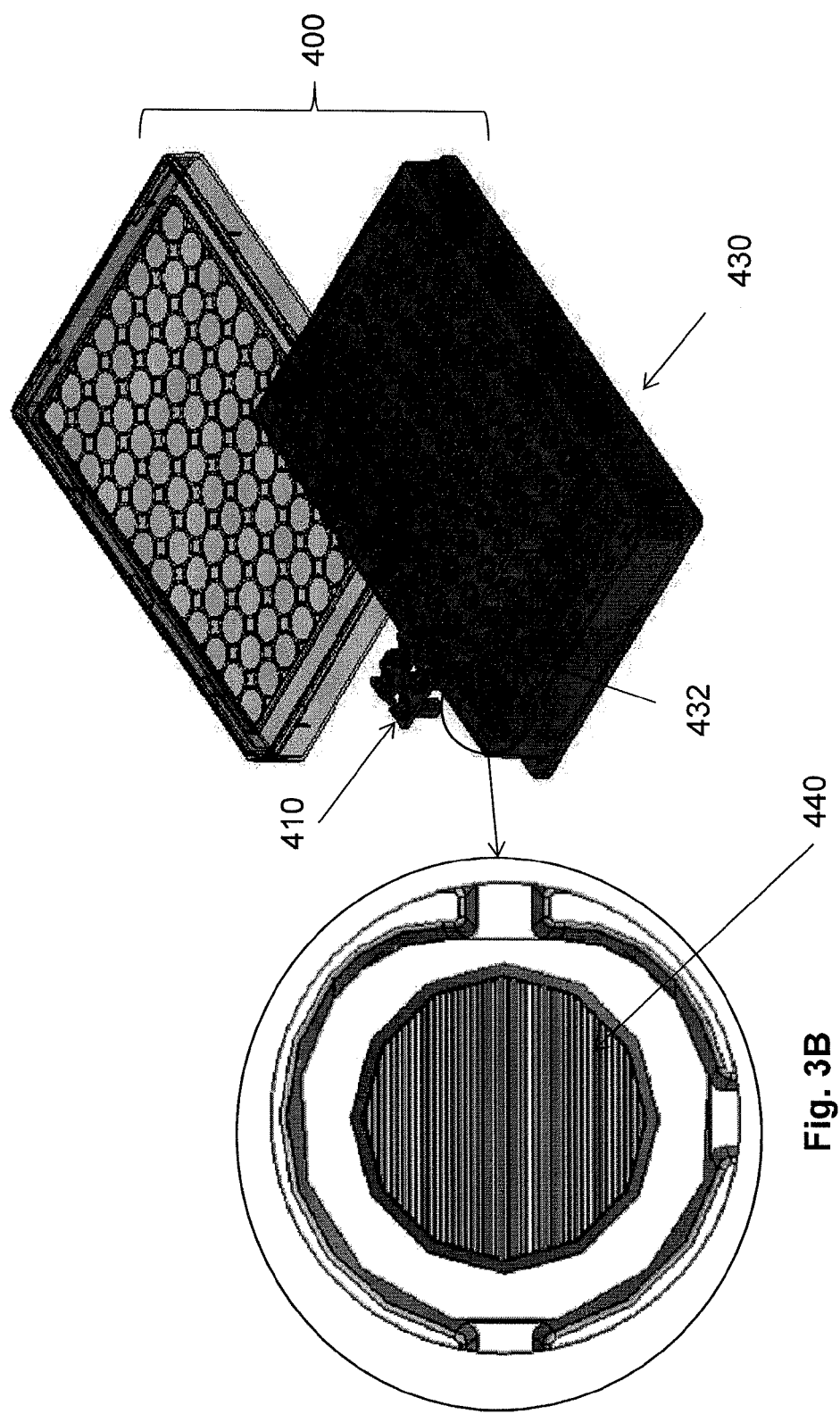
FIG. 3B is a schematic representation of an example of a co-culture device assembly 400, including a an insert tray 410 for insertion into a multi-well plate 430, where the wells of the multi-well plates comprise microelectrode structures 440. Here a 16-well chamber insert tray 410 and a 96-well plate 430 are shown.

FIG. 3A shows a schematic representation of an example of a co-culture device assembly 300, including a multi-chamber insert tray 310 for insertion into a multi-well plate 330, where the wells 332 of the multi-well plate 330 include microelectrode structures 340. Here a 16-well chamber insert tray 310 and a 16-well plate 330 are shown. FIG. 3B shows a schematic representation of an example of a co-culture device 400, comprising a multi-chamber insert tray 410 for assembly with a multi-well plate 430, where the wells 432 of the multi-well plate 430 include microelectrode structures 440. Here six 16-well chamber insert trays 410 and a 96-well plate 430 are shown.

Method of Use of Co-Culture Devices of the Present Invention

In yet another aspect, the invention is directed to a method of culturing and monitoring cells using the co-culture device assembly of the present invention. The method includes the following steps, providing a co-culture device assembly of the present invention for culture of different types of the cells, including a multi-well plate and an insert tray including multiple insert chambers, adding one type of cells to the wells of the multi-well plates, adding another type of cells into the insert chambers of the insert trays, inserting or assembling the insert tray with the multi-well plate, and monitoring the cells cultured in the device assembly.

Further, the methods can also assess the effect of one or more compounds on the co-culture. That is, compounds can be added to either the upper or lower chambers to assess stimulation, inhibition, increasing or decreasing sensitivity and the like. In addition, cellular responses to particular doses or dose ranges can be assessed.

In one embodiment, monitoring cells includes imaging cells cultured in wells of the multi-well plate at different time points of cell culture. In another embodiment, monitoring cells includes conducting a WST or MTT assay to monitor viable cell numbers in the wells of multi-well plate, such as at the end of the assay. In another embodiment, the wells of the multi-well plate include microelectrode arrays that can be used for monitoring cells grown on the electrodes and monitoring the cells includes measuring electrode impedances when cells are cultured in the multi-wells at single or multiple time points.

The cells being added to the wells of the multi-well plates may include any cells of interest. Typically target cells, or cells that are affected by other cells are added to the wells. Examples include mammalian cell lines, cancer cells, normal cells, primary cells, and the like. The cells can have different tissue origin, such as lung cancer cells, breast cancer cells, hepatocytes, neuronal cells, cardiomyocytes, fibroblast cells, or the like. The cells can be added into the wells together with cell culture media suitable for growth or proliferation or survival of the cells.

In another embodiment, the cells being added into the insert chambers of the insert trays may include any cells of interest. Typically, effector cells or cells that affect other cells are added to the insert chamber. Examples of these cells are mammalian cell lines, cancer cells, normal cells, primary cells, and the like. The cells can have different tissue origin, such as lung cancer cells, breast cancer cells, hepatocytes, neuronal cells, cardiomyocytes, fibroblast cells, etc. The cells can be added into the insert chambers together with cell culture media suitable for growth or proliferation or survival of the cells.

In one embodiment, the insert tray is assembled with the multi-well plate after the cells have been added to the wells of the multi-well plate but prior to the cell addition to the insert chambers. In another embodiment, the insert tray is assembled with the multi-well plate after the cells have been added to the wells of the multi-well plate and after the cell addition to the insert chambers.

Cells cultured in the wells of the multi-well plate can be monitored using different means. In one embodiment, monitoring cells includes imaging the cells cultured in the wells of the multi-well plate at different time points of cell culture. In another embodiment, monitoring the cells includes conducting WST or MIT assays to monitor viable cell numbers in the wells of multi-well plate at the end of the assay. In another embodiment, the wells of said multi-well plate comprise microelectrode arrays that can be used for monitoring cells grown on the electrodes and monitoring the cells comprises the measurement of electrode impedances when the cells are cultured in the multi-wells at single or multiple time points.

D. EXAMPLES

The insert device or insert tray of the present invention is preferably a single-use cell culture disposable. It can be used in conjunction with the micro-titer multi-well plate to examine the indirect interactions between two different cell lines or cell types, with one cell type (target cells) cultured in the wells of the micro-titer plate, and the other cell type (effector cells) cultured in the insert chambers of the insert device/tray. The combination of the insert device/tray and the micro-titer multi-well plate enables the investigation of indirect cell-cell interactions, such as paracrine signaling affecting cell proliferation, cell survival, cell adhesion, and cellular morphological changes. Such paracrine signaling effect can be measured or monitored by different readouts, including end-point assay readouts (e.g. MTT based assays using plate reader and imaging based readout) in regular micro-titer plates and imaging of the cells at single or multiple time points in regular micro-titer plates.

In preferred embodiments, the cells in the multi-well plate can be monitored using real-time, label-free measurement with impedance technology in E-PLATE devices (ACEA Biosciences Inc., San Diego Calif., and Roche applied sciences). FIG. 5A shows a schematic representation of an exemplary co-culture assay with impedance measuring capabilities. The co-culture system includes a co-culture device assembly including a top chamber 602 including a porous bottom 616 and a bottom chamber 604 including electrode structures 640. The top chamber 602 (defined by a chamber insert) is assembled into the lower chamber 604 to form the co-culture device assembly. Effector cells 650 are cultured on the porous bottom 616 of top chamber 602 and target cells 652 are cultured on the electrode surfaces 640 of the lower chamber 640. In the example shown in FIG. 5A, the target cells 652 cultured in the lower chamber 604 are monitored with an impedance sensing system (Roche Applied Sciences and ACEA Biosciences) including an impedance analyzer 710, an E-PLATE station 700 which provides mechanical and electronic interfaces between E-PLATES and the impedance analyzer 710, and a computer 720 with software that can communicate with and control the impedance analyzer 710 and E-PLATE station 700. Molecules from the top chamber 602 secreted or produced by the effector cells 650 are permitted to pass through the pores of the porous bottom 616 to reach the bottom chamber 604 thereby potentially producing a biological effect on the target cells 652. In one option, stimulant molecules 651 are applied to the top chamber 602 to stimulate the effector cells 650 to produce/release molecules upon stimulation. The released molecules from effector cells 650 pass through the pores on the porous bottom 616 to reach the lower chamber 604 to produce a biological effect on the target cells 652.

FIG. 5B shows schematic representations of three types of co-culture effects: stimulation, toxicity and modulation, as monitored with impedance electrode sensing structures and shown with cell index as a readout. The broken lines show the time-dependent curves for the target cells cultured alone whilst the solid lines show those when the target cells are co-cultured with the effector cells in a co-culture setup. For such schematic representations, stimulation indicates that the target cells exhibit increased electrical impedance signals, toxicity indicates that the target cells exhibit decreased electrical impedance signals, modulation indicates that target cells exhibit "down-then-up" electrical impedance signals, under the influences of the effector cells.

Several examples of co-culture assays using the devices and methods of the present invention are described below to examine steroid hormone signaling and tumor-stroma interactions through indirect cell-cell co-culture. Target cells are cultured in micro-titer multi-well plates, and effector cells are cultured in insert chambers. When insert chamber of the insert trays are placed in the wells with target cells, the effect of cell-cell interactions can be measured.

For the steroid hormone signaling application, the human ductal breast epithelial tumor cell line T47D, which expresses receptors for a variety of steroid hormones (e.g. estrogen and progesterone), is cultured on a micro-titer multi-well plate as the target cells. The human female adrenocortical carcinoma cell line NCI-H295R, which expresses various steroid hormones (including estrogen and progesterone), is cultured on the insert tray and used as effector cells. When the insert tray is combined with the micro-titer plate, the steroid hormones synthesized and secreted by NCI-H295R cells in the insert tray binds to receptors in T47D cells in the micro-titer plate and initiate its downstream signal transduction pathways, affecting T47D cell growth/proliferation. This growth-stimulating effect on T47D cells were measured and documented by end-point WST-1 assay and imaging analysis in regular micro-titer plate, and also continuous real-time label free monitoring in E-Plate using xCELLigence platform (ACEA Biosciences Inc., San Diego, Calif. and Roche Applied Science).

For tumor stroma interactions, examples concerning interactions between fibroblast/tumor and tumor/endothelial cells are described. Tumor-associated fibroblasts often secrete growth factors to promote tumor cell proliferation and/or survival. In one example, the lung fibroblast cell line MRC-5 is cultured in the insert tray as effector cells, and human pancreatic cell line BxPC3 is cultured in multi-well 96x E-PLATE. Combination of the insert trays with E-PLATE allows continuous real-time label-free monitoring of MRC-5 effect on BxPC3 cell proliferation. In another example, the lung fibroblast cell line MRC-5 is cultured in the insert as effector cells, and human non-small cell lung (NSCL) cancer cell line HCC827 is cultured on E-PLATE. Hepatoma derived growth factor (HGF) secreted by MRC-5 mediated short-term morphological change of HCC827, and long-term HCC827 survival when treated with anti-cancer therapy (EGFR small molecule inhibitor Gefitinib), that was documented by impedance measurement continuously in real-time.

Another example of tumor stroma interaction concerns tumor/endothelial cells. Tumor cells secrete growth factors to promote endothelial cell proliferation, morphogenic changes, migration, and eventually results in new blood vessel formation (angiogenesis). In this example, human glioblastoma cancer cell line U87 is cultured in the insert tray, and primary human umbilical vein endothelial cells (HUVEC) are cultured in the multi-well 96x E-PLATE. Growth factor secreted by U87 cells mediates short-term morphological change and long-term proliferation of HUVEC cells, that are monitored by impedance measurement.

In addition to co-culture assay applications listed above, the devices and the methods of the present invention can also be used to examine immune-regulation, inflammation, stem cell proliferation and differentiation, transplantation, neurology and barrier function, to name a few.

Example 1

Co-Culture Assay Application in Steroid Hormone Signaling

T47D/H295R Assay in Micro-Titer Plate Using WST-1 Readout

Cell Lines.

T47D, a human ductal breast epithelial tumor cell line, expresses receptors for a variety of steroid hormones, including estrogen and progesterone. NCI-H295R, a human female adrenocortical carcinoma cell line, expresses various steroid hormones (including estrogen and progesterone).

Both cell lines pre-cultured in media containing 10% charcoal treated FBS for 3-4 days were used for the experiment. 10,000 T47D cells were seeded onto the multi-well 96x E-PLATE in media containing 10% charcoal treated FBS. Different numbers of NCI-H295R cells were seeded into 16x insert trays in media containing 10% charcoal treated FBS (8,000 cells/well, 4,000 cells/well, 2,000 cells/well, 0 cells/well). 24 hours later, the insert trays were placed in E-PLATE wells, and put in 37° C. incubator with 5% $CO^2$ for four additional days. At the end of experiment, the insert trays were removed and T47D culture media was replaced with fresh media containing 10% WST-1 reagents. After 2-4 hours incubation at 37° C. incubator, T47D media with WST-1 reagent was transferred to a regular 96-well plate, and absorbance at 450 nm was measured using a plate reader. In addition, both T47D cells on E-PLATE and NCI-H295R cells in the insert trays were subject to Diff-quik staining, and images taken under microscope.

Figures 6A, 6B:
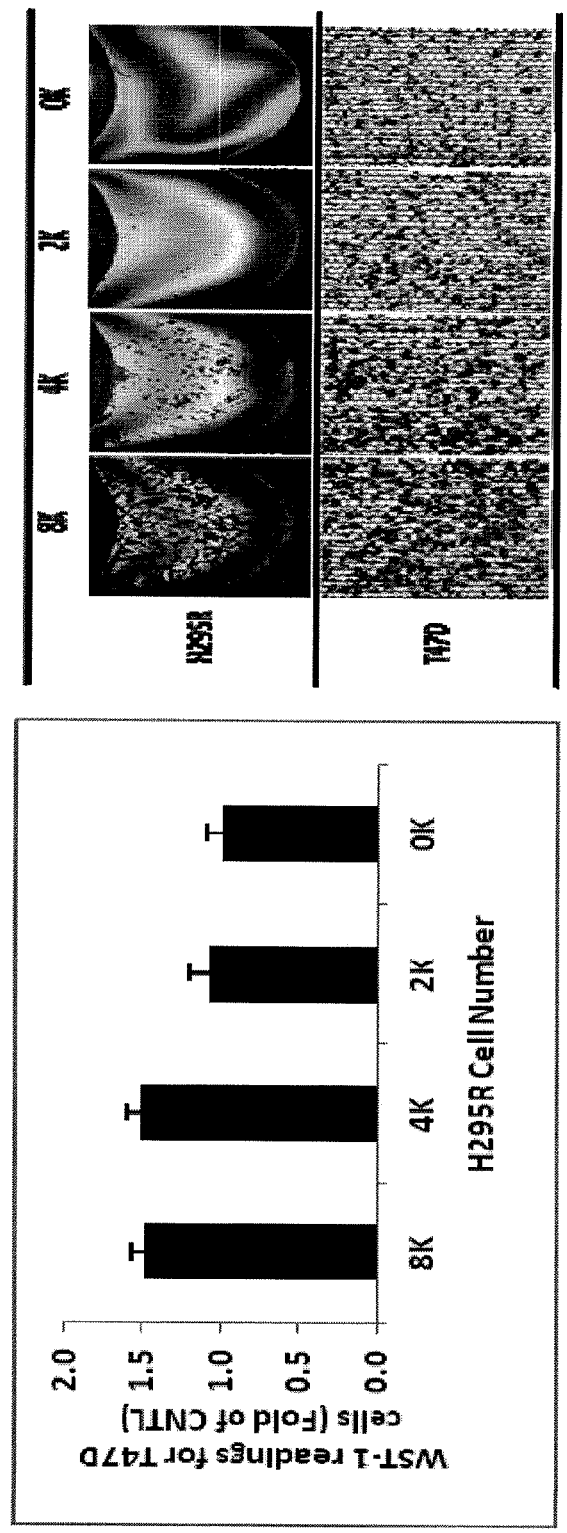
FIG. 6A is a chart showing WST-1 assay results for T47D cells. Higher WST-1 reading was observed for higher NCI-H295R seeding numbers.
FIG. 6B is a picture depicting the imaging of T47D cells on 96x E-Plate where more T47D cells were observed when more NCI-H295R cells were cultured in the insert tray.

FIG. 6A shows the WST-1 assay results for T47D cells, and the higher WST-1 reading was observed for higher NCI-H295R seeding numbers. As WST-1 assay measures cellular metabolic activity and correlates with cell number, factors secreted by NCI-H295R cells in the insert tray increased T47D proliferation in a dose-dependent manner. The proliferation effect documented by WST-1 readings was also confirmed by Diff-quik staining results, as more T47D cells on 96x E-Plate were observed when more NCI-H295R cells were cultured in the insert tray (FIG. 6B).

Example 2

Co-Culture Assay Application in Steroid Hormone Signaling

T47D/H295R Assay in Micro-Titer Plate Using Imaging Readout

Cell Lines.

T47D, a human ductal breast epithelial tumor cell line, expresses receptors for a variety of steroid hormones, including estrogen and progesterone. NCI-H295R, a human female adrenocortical carcinoma cell line, expresses various steroid hormones (including estrogen and progesterone).

Figure 7A:
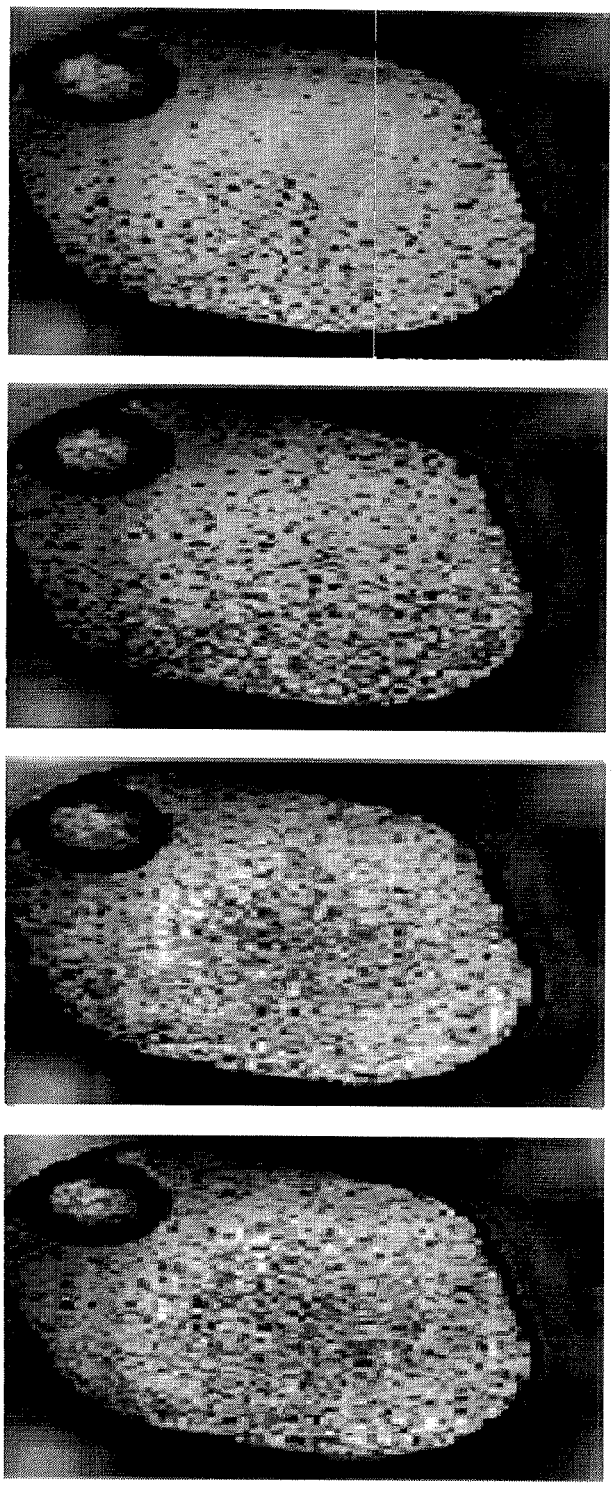
FIG. 7A shows images of T47D cells at the end of experiment. More T47D cells were observed when higher NCI-H295R cells were cultured in the Insert chamber, in a dose-dependent manner.
Figure 7B:
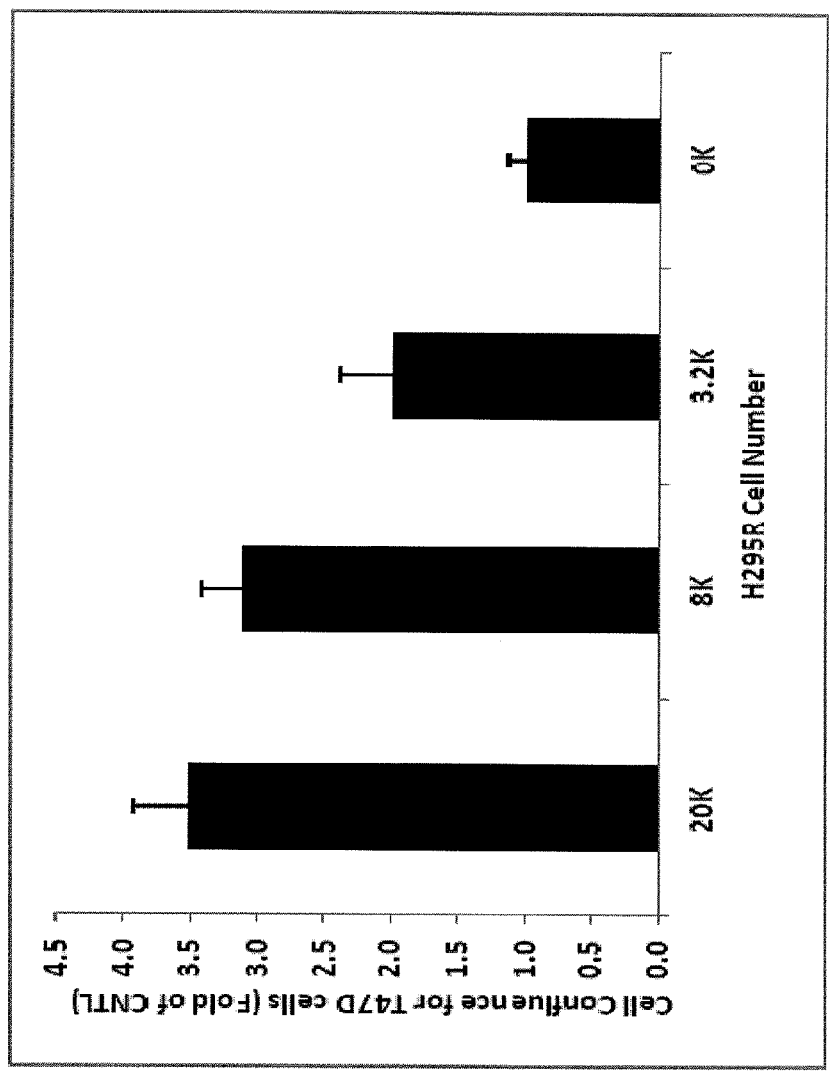
In FIG. 7B a chart is showing that depicts the number of T47D cells can be quantified and represented as the percentage of confluence by the Cellavista software, which is consistent with the images shown in FIG. 7A.

Both cell lines pre-cultured in media containing 10% charcoal treated FBS for 3-4 days are used for the experiment. 10,000 T47D cells are seeded onto micro-titer plate (Corning) in media containing 10% charcoal treated FBS. Different numbers of NCI-H295R cells are seeded into 16x insert trays of the present invention in media containing 10% charcoal treated FBS (20,000 cells/well, 8,000 cells/well, 3,200 cells/well, 0 cells/well). 24 hours later, insert trays were placed in wells of the micro-titer plate, and put in 37° C. incubator with 5% $CO_2$ for six additional days. At the end of experiment, insert trays were removed and T47D cells were subject to Diff-quik staining. Stained T47D cells in the micro-titer plate were put in Cellavista instrument (Roche Applied Sciences) for imaging analysis. FIG. 7A shows that factors secreted by NCI-H295R cells in the insert tray increased the T47D proliferation in a dose-dependent manner, as more T47D cells were observed when higher NCI-H295R cells were cultured in the insert tray. In addition, number of T47D cells can be quantified and represented as the percentage of confluence by the Cellavista software (FIG. 7B), that again confirmed the imaging results that NCI-H295R dose-dependently increased T47D cell proliferation.

Example 3

Co-Culture Assay Application in Steroid Hormone Signaling

T47D/H295R Assay with E-PLATE Using Continuous Impedance Readout

Cell Lines.

T47D, a human ductal breast epithelial tumor cell line, expresses receptors for a variety of steroid hormones, including estrogen and progesterone. NCI-H295R, a human female adrenocortical carcinoma cell line, expresses various steroid hormones (including estrogen and progesterone).

Figure 8A:
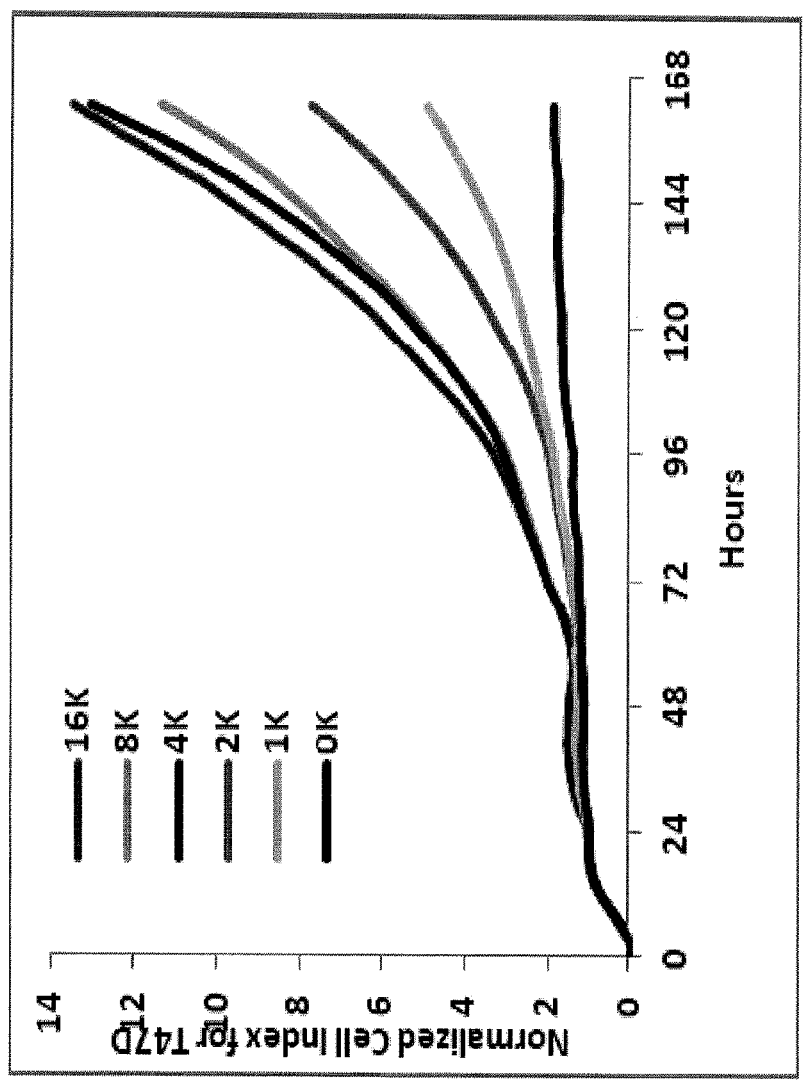
FIG. 8A is a chart showing the Cell Index curves for T47D cells that were continuously monitored for the entire duration of the experiment. Higher Cell Index readings were observed when more NCI-H295R cells were cultured in the insert tray.
Figure 8B:
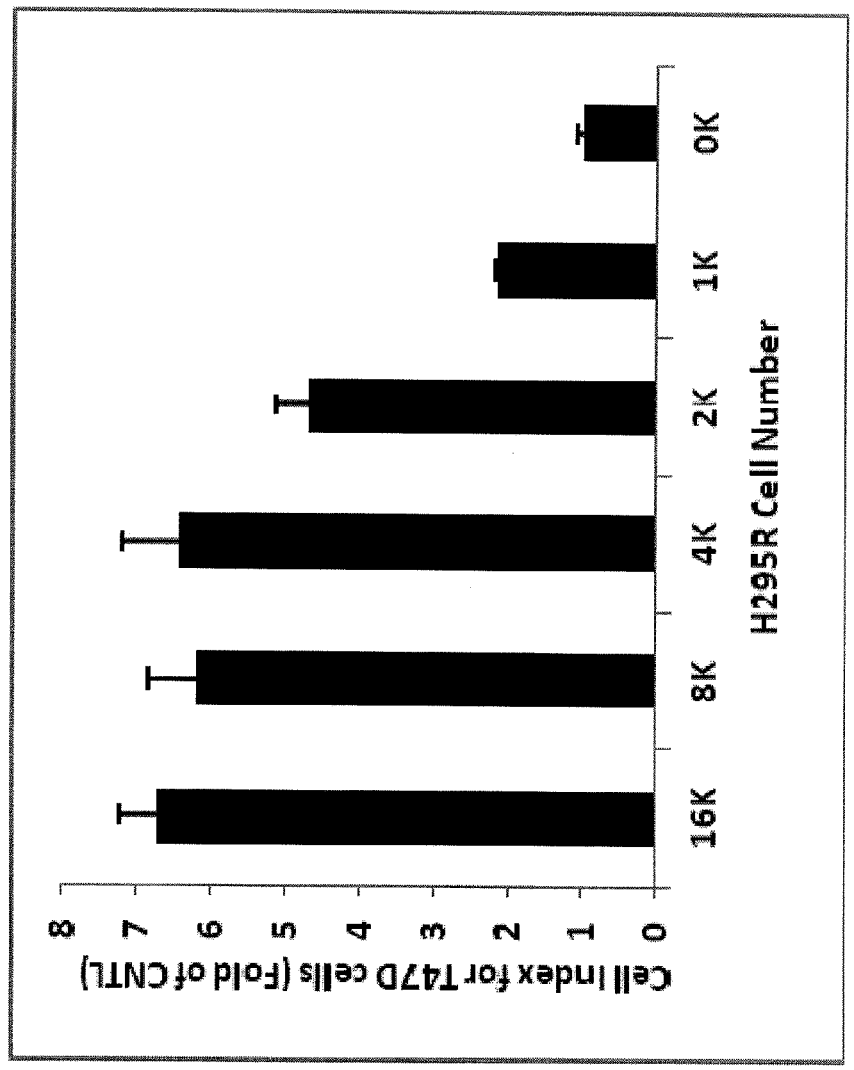
FIG. 8B is a chart showing Cell Index readings for T47D cells at the end of experiment. Higher Cell Index was observed when higher H295R cells were seeded in the insert tray.
Figure 8C:
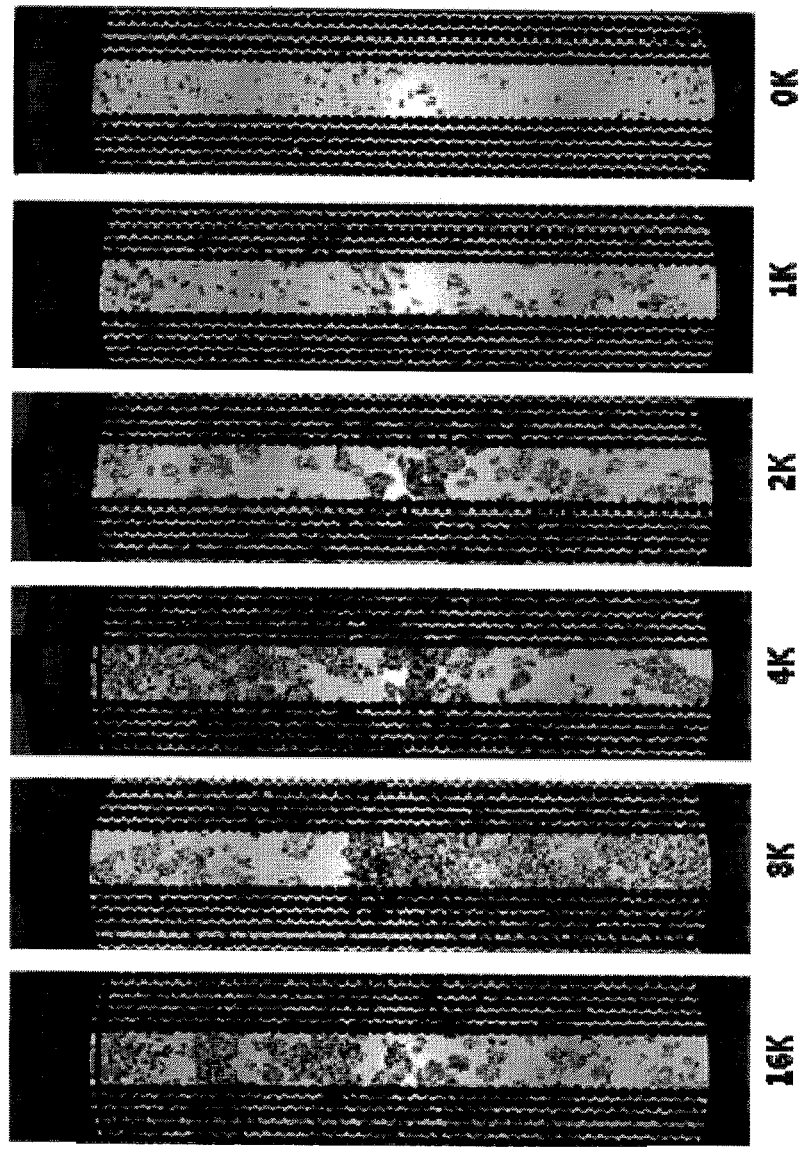
FIG. 8C is a series of images showing the number of T47D cells in the view area of E-Plate View at the end of experiment using Cellavista instrument. More T47D cells were observed when more H295R cells were seeded in the insert tray.

Both cell lines pre-cultured in media containing 10% charcoal treated FBS for 3-4 days are used for the experiment. 4,000 T47D cells are seeded onto multi-well 96x E-PLATE (Roche applied sciences) in media containing 10% charcoal treated FBS. Different numbers of NCI-H295R cells are seeded into 16x insert trays in media containing 10% charcoal treated FBS (16,000 cells/well, 8,000 cells/well, 4,000 cells/well, 2,000 cells/well, 1,000 cells/well & 0 cells/well). 24 hours later, insert trays were placed in 96x E-PLATE, and put in RTCA station in 37° C. incubator with 5% $CO_2$ for six additional days. T47D cell proliferation (Cell Index) is monitored continuously in real-time for the entire duration of the experiment (FIG. 8A). At the end of experiment, insert trays were removed and T47D cells were subject to Diff-quik staining. Stained T47D cells in the E-Plate were put in Cellavista instrument (Roche Applied Sciences) for imaging analysis. FIGS. 8B & 8C show that factors secreted by NCI-H295R cells in the insert tray increased the T47D proliferation in a dose-dependent manner, as higher Cell Index (FIG. 8B) and more T47D cells (FIG. 8C) were observed when higher NCI-H295R cells were cultured in the insert tray.

Example 4

Co-Culture Assay Application in Tumor-Stroma Interaction

BxPC3/MRC-5 Assay with E-PLATE Using Continuous Impedance Readout

Cell Lines.

BxPC3 is a human pancreatic cancer cell line, and MRC-5 is a lung fibroblast cell line.

Figure 9:
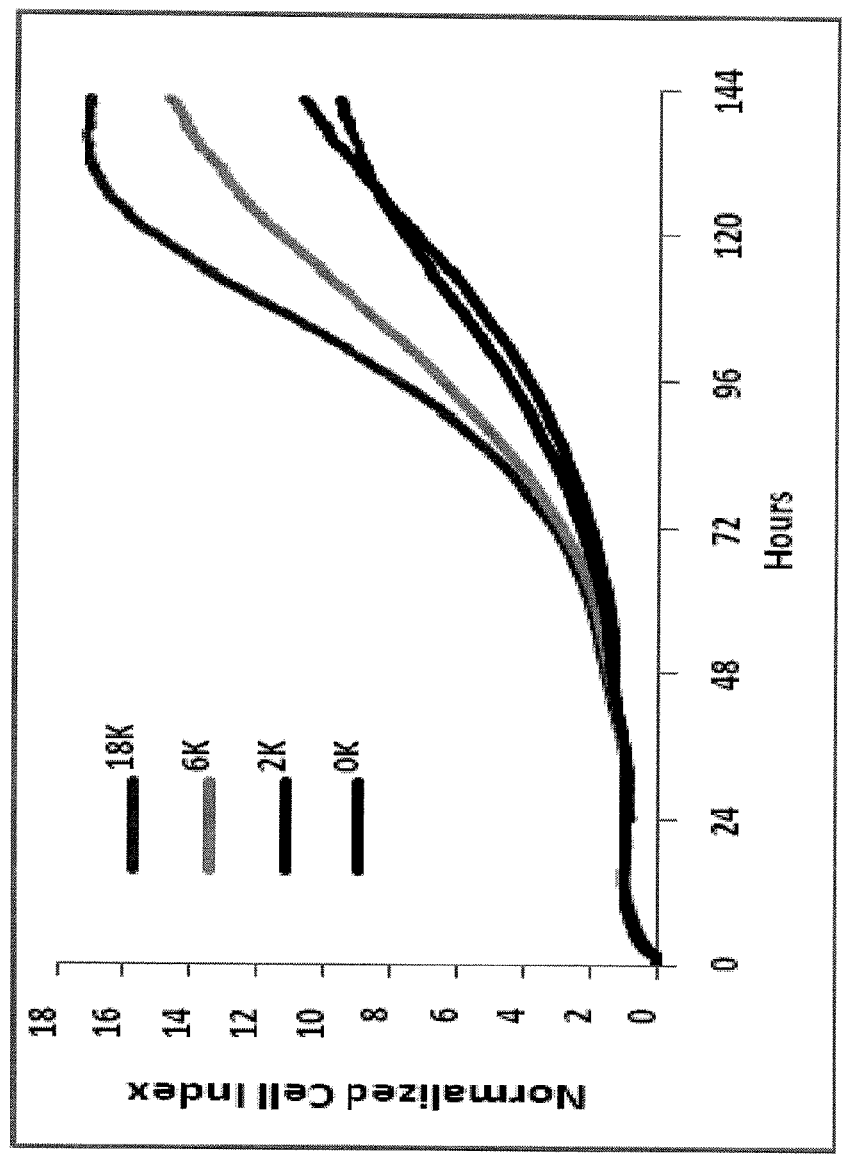
FIG. 9 is a chart showing the Cell Index curves for BxPC3 cells that were continuously monitored for the entire duration of the experiment. Higher Cell Index readings were observed when more MRC-5 cells were cultured in the insert tray.

Both cell lines pre-cultured in media containing 10% charcoal treated FBS for 3-4 days were used for the experiment. 1,250 BxPC3 cells were seeded onto E-PLATE (Roche applied sciences) in media containing 5% charcoal treated FBS. Different numbers of MRC-5 cells were seeded into 16x insert trays in media containing 5% charcoal treated FBS (18,000 cells/well, 6,000 cells/well, 2,000 cells/well, & 0 cells/well). 24 hours later, Inserts were placed in E-PLATE, and put in RICA station in 37° C. incubator with 5% $CO_2$ for five additional days. BxPC-3 cell proliferation (Cell Index) was monitored continuously in real-time for the entire duration of the experiment. FIG. 9 showed that factors secreted by MRC-5 cells in the insert tray increased the BxPC-3 proliferation in a dose-dependent manner, as higher Cell Index (FIG. 9) was observed when higher MRC-5 cells were cultured in the insert tray.

Example 5

Co-Culture Assay Application in Tumor-Stroma Interaction

HCC827/MRC-5 Drug Resistance to Gefitinib Assay with E-Plate Using Continuous Impedance Readout Cell Lines and Reagents.

HCC-827 is a human non-small cell lung cancer (NSCL) cell line that expresses a constitutively active mutant EGFR protein (Exon 19 deletion, ΔL747-S752), and therefore is sensitive to EGFR inhibitors, including small molecule inhibitor Gefitinib. MRC-5 is a lung fibroblast cell line that secretes human hepatoma derived growth factor (HGF).

Figure 10A:
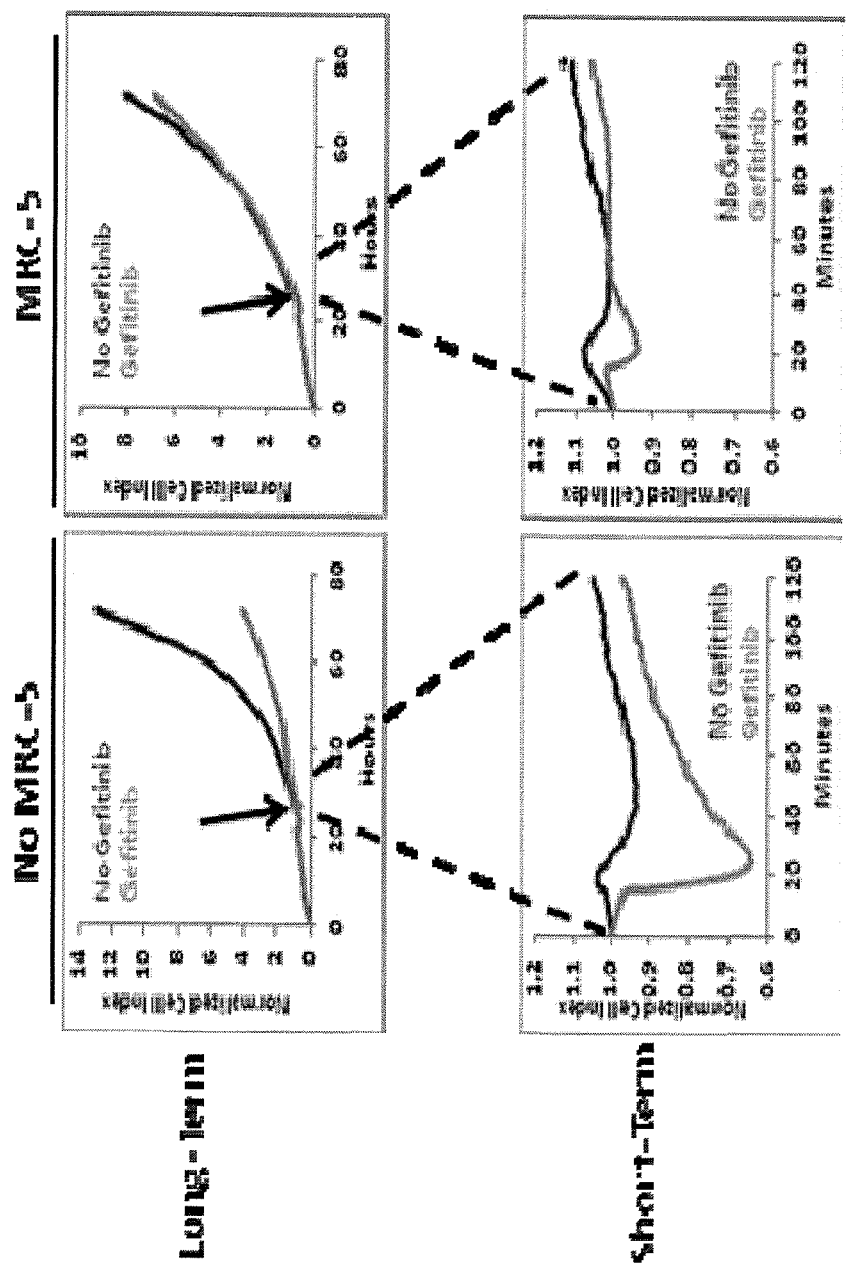
FIG. 10A shows charts depicting that in the absence of MRC-5 cells in the insert tray, small molecule EGFR inhibitor gefitinib mediated cytotoxic effect to HCC827 cells, and the long-term cytotoxic effect correlated with the short-term Cell Index changes (decrease followed by recovery).
Figure 10B:
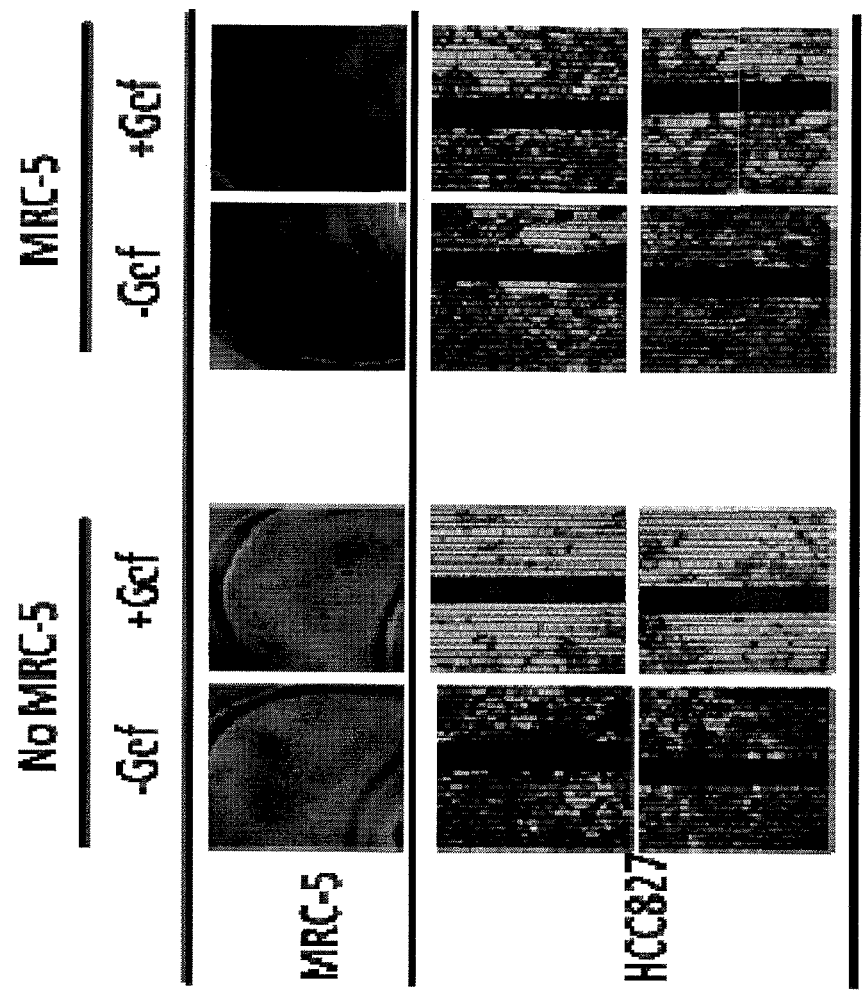
FIG. 10B shows optical images showing that in the presence of MRC-5 cells in the insert tray, HCC827 became resistant to gefitinib, which is consistent with the loss of short-term Cell Index changes. Also in FIG. 10B the long-term HCC827 Cell Index changes in responses to gefitinib is consistent with the imaging results at the end of experiment. The presence of MRC-5 mediated HCC827 resistance to gefitinib treatment.

For the experiment, 1,000 HCC827 cells were seeded into multi-well 96x E-PLATE (Roche applied sciences). 40,000 or 0 MRC-5 cells were seeded in 16x insert trays. 24 hours later, 16x insert trays were placed in 96x E-Plate, and put in RTCA station in 37° C. incubator with 5% $CO^2$ for several hours, with Cell Index monitored every 15 minutes. E-PLATE with the insert tray was then removed from the station, and Gefitinib was added to half of the E-PLATE wells through the access port, with the other half used as no-Gefitinib controls. Cell Index was monitored for two to three additional days (FIG. 10A). At the end of experiment, both HCC827 cells on the E-PLATE and MRC-5 cells in the insert tray were subject to Diff-quik staining, and images taken under the microscope (FIG. 10B).

FIG. 10A shows that HCC827 growth was inhibited by Gefitinib in the absence of MRC-5 in the insert tray. However, the presence of MRC-5 cells in the insert tray cause HCC827 to become resistant to Gefitinib treatment. This effect is consistent between Cell Index measurement (FIG. 10A) and imaging (FIG. 10B). In addition, a short-term cell index change in response to gefitinib (Cell Index decrease followed by Cell Index recovery) correlates well with long-term growth inhibition of HCC827 cells. In the absence of MRC-5 in the insert tray, Gefitinib mediates a short-term Cell Index change (Cell Index decrease, followed by recovery, FIG. 10A, bottom panel), followed by a long-term growth inhibition (FIG. 10A, top panel). In the presence of MRC-5 cells in the insert tray, the short-term Cell Index change was abolished (FIG. 10A, bottom panel), and this is consistent with the minimal long-term effect mediated by Gefitnib (FIG. 10A, top panel).

Figure 10C:
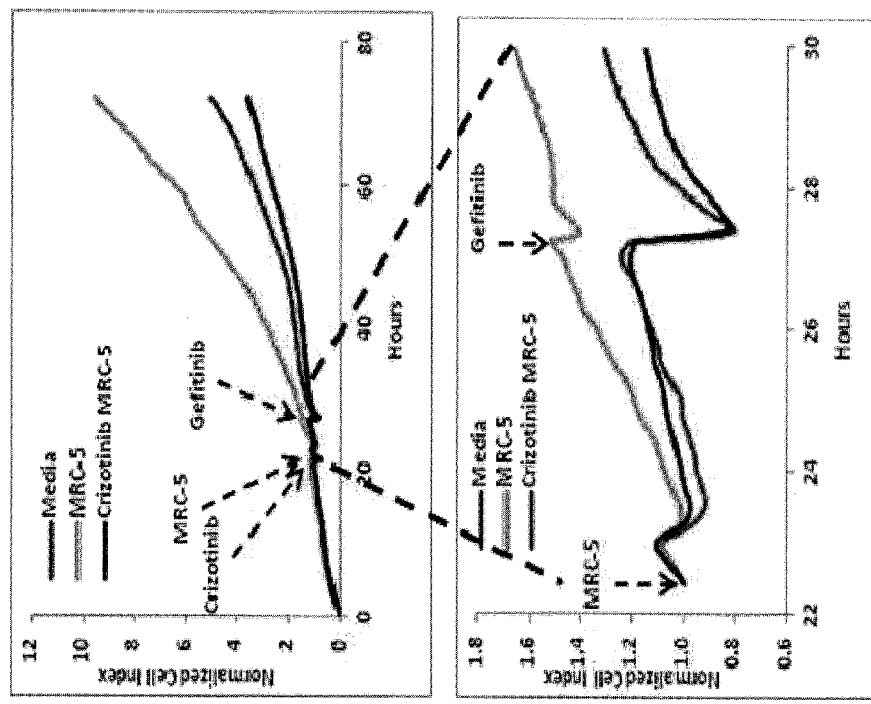
FIG. 10C is a chart depicting short-term responses of HCC827 in response to MRC-5 and gefitinib can be monitored by Cell Index changes. The presence of MRC-5 mediated a short-term Cell Index increases of HCC827, and abolished gefitinib mediated short-term (Cell Index decrease followed by recovery) and long term cytotoxic effect (green). The addition of cMet inhibitor crizotinib inhibited MRC-5 mediated short-term Cell Index increase, and restored gefitinib mediated short-term (Cell Index decrease, followed by recovery) and long-term cytotoxic responses.

Furthermore, MRC-5 mediates HCC827 resistance to Gefitinib treatment through HGF signaling pathway. HGF secreted by MRC-5 binds to its receptor cMet on HCC827 and activates its down-stream signaling pathway, e.g. PI3K, and causes a short-term morphological change that is characterized by a short-term Cell Index increase. The activation of PI3K, which is downstream of EGFR, bypasses requirement for EGFR, and cause resistance to EGFR inhibitors. The HGF signaling pathway can be blocked by cMet inhibitor Crizotinib. The presence of Crizotinib abolished MRC-5 (HGF) mediated short-term responses and restored Gefitinib mediated short-term (Cell Index decrease followed by recovery) and long-term (growth inhibition) cell index responses (FIG. 10C, top panel).

Example 6

Co-Culture Assay Application in Tumor-Stroma Interaction

HUVEC/U87 Assay with E-PLATE Using Continuous Impedance Readout

Cell Lines:

U87 is a human glioblastoma cancer cell line which is reported to secrete vascular endothelial growth factor. HUVEC are primary human umbilical vein endothelial cells.

Figure 11A:
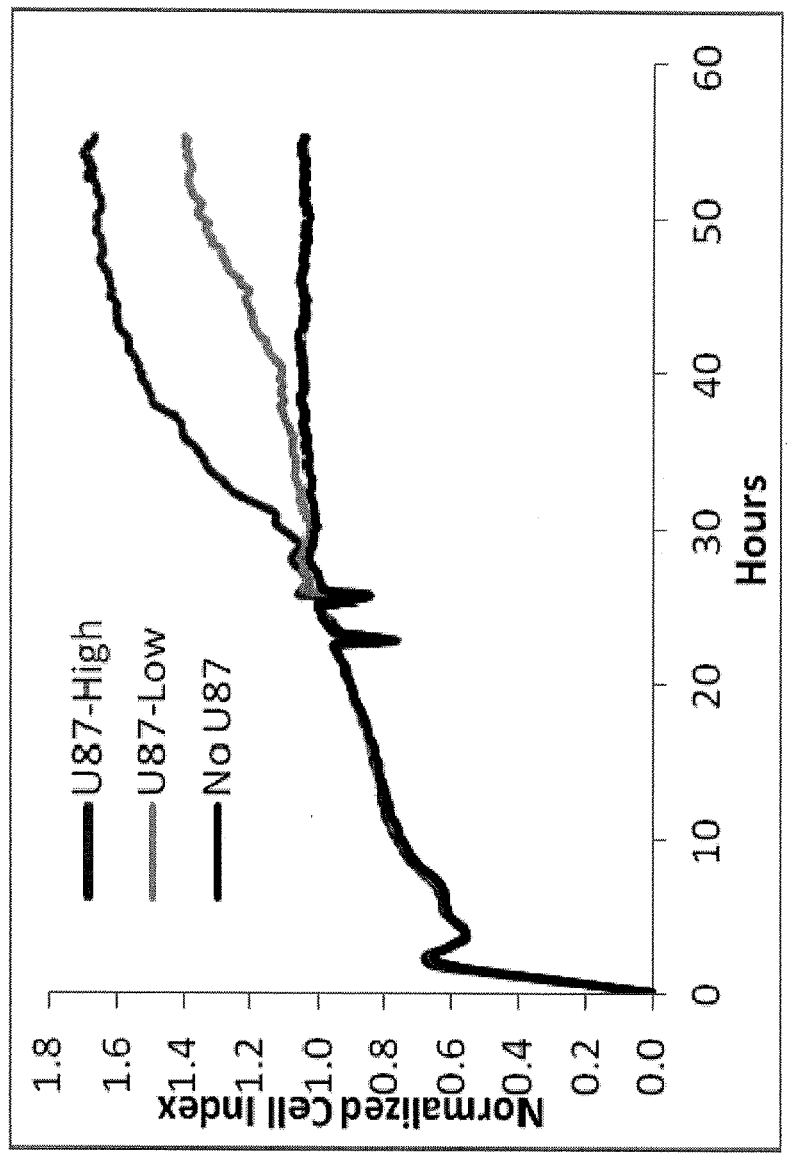
FIGS. 11A-C show charts showing Cell Index curves for HUVEC cells that were monitored continuously for the entire duration of the experiment. Higher Cell Index was observed when higher numbers of U87 cells were seeded in the insert tray.
Figure 11B:
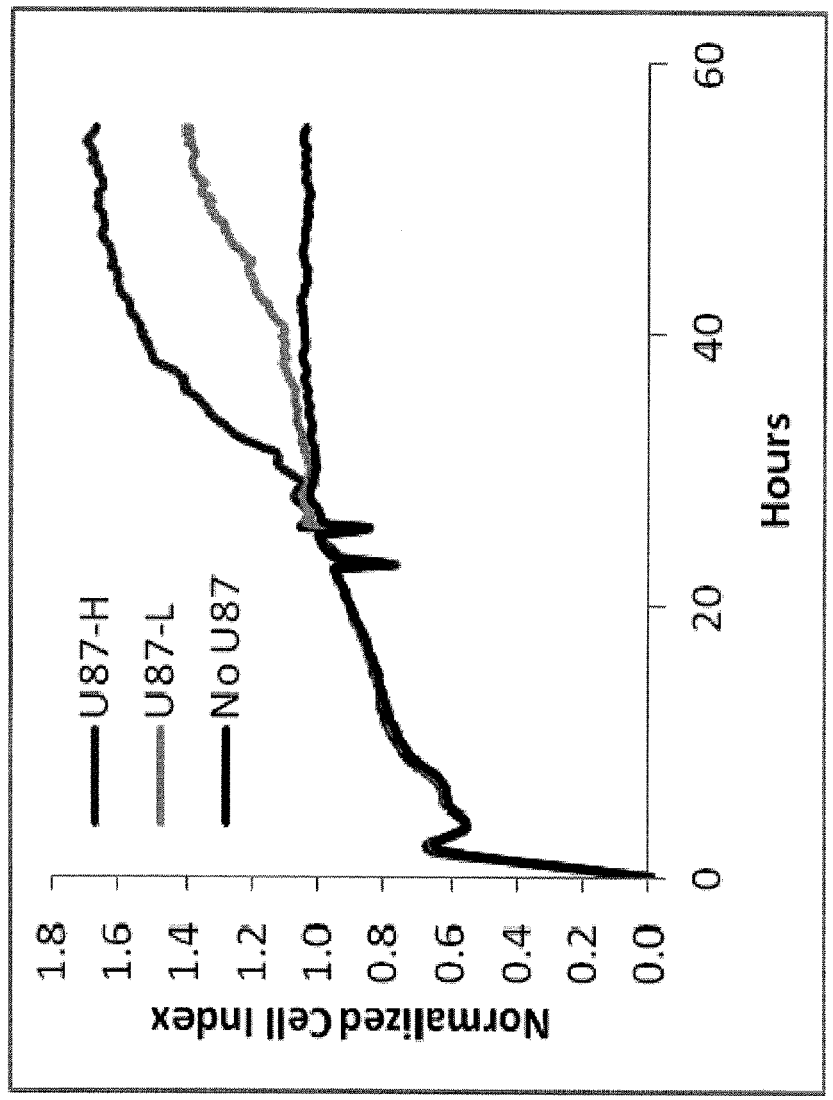
Figure 11C:
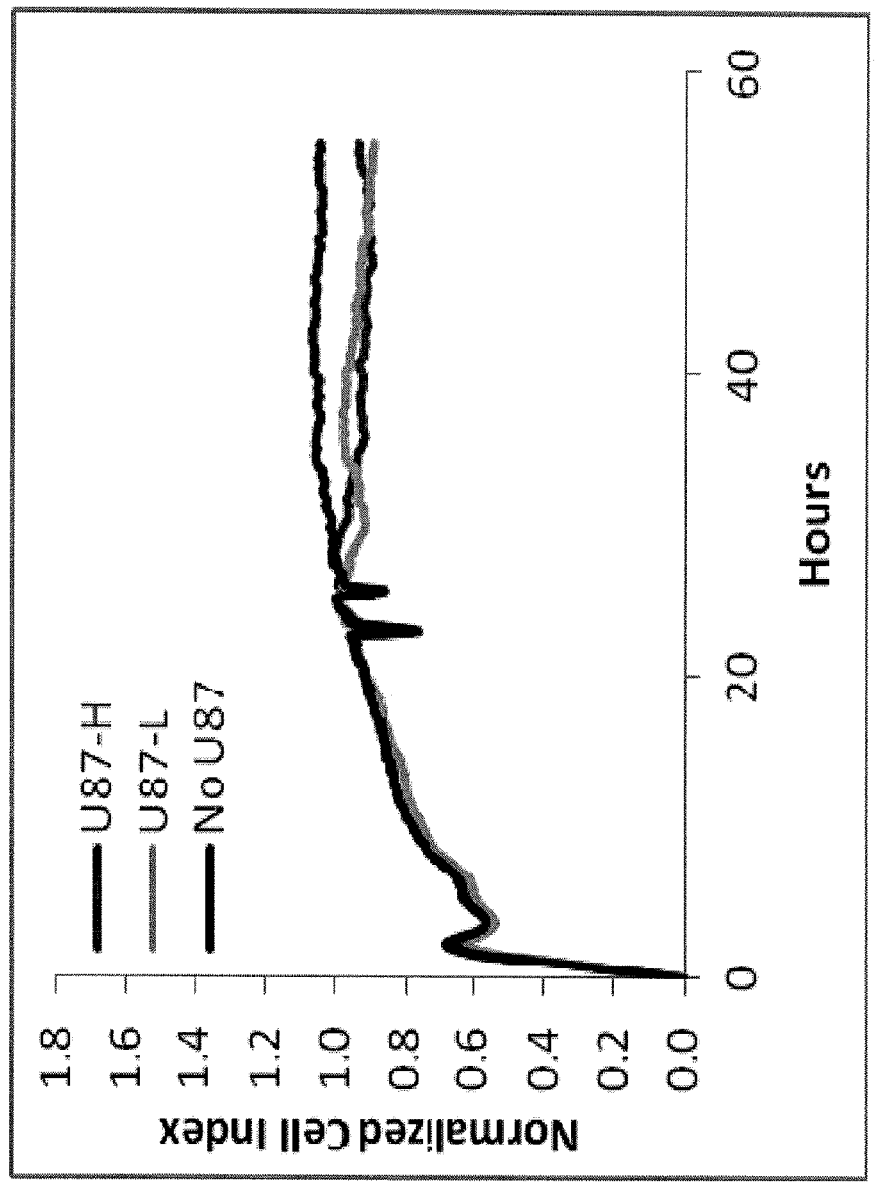

For the experiment, U87 is cultured in the 16x insert trays at three seeding densities (30,000 cells/well, 10,000 cells/well, and 0 cells/well). HUVEC cells are seeded in multi-well 96x E-PLATE at 3,000 cells/well. 24 hours later, vehicle control (FIG. 11A), control IgG (FIG. 11B), and neutralizing mAb against VEGF (FIG. 6C) were added to HUVEC cells before insert trays were placed in the 96x E-PLATE, and put in RTCA station in 37° C. incubator with 5% $CO^2$ for two additional days. HUVEC Cell Index is monitored continuously in real-time for the entire duration of the experiment. FIG. 11A showed that factors secreted by U87 cells in the insert trays mediated both short-term morphological changes and long-term increased proliferation in a dose-dependent manner, as higher Cell Index changes (FIG. 11A) were observed when more U87 cells were cultured in the insert tray. In addition, this effect is mediated through VEGF secreted by U87, as the stimulatory effect was blocked by VEGF neutralizing antibody (FIG. 11C), but not by a control IgG (FIG. 11B).

What is claimed is:

1. A co-culture device assembly comprising an insertion device suspended above a bottom surface of a well to form an upper chamber for housing cells over a lower chamber, wherein the insertion device is characterized as:
    a) an insert chamber comprising two fluid impermeable side walls extending from a microporous bottom to an open top to form an inner cavity, characterized in that first and second side walls are each shaped convex and are joined to one another at each end, wherein the first and second side walls are of a same height; and
    b) a flange extending outward from or beneath the top of the insert chamber and suspending the microporous bottom above the bottom surface of the well to form the upper and lower chambers, the flange notched to form a gap providing access to the lower chamber but not the top chamber, wherein a bottom surface of the flange comprises an upward extending recess that recesses into the flange for preventing or reducing liquid migration across the bottom surface of the flange.

2. The assembly according to claim 1, wherein the flange follows the perimeter of the first sidewall.

3. The insert device according to claim 1, wherein the open top comprises an outer ridge extending above the flange.

4. The insert device according to claim 1, wherein the two side walls taper from top to bottom.

5. The insert device according to claim 1, wherein the microporous bottom comprises a porous biocompatible membrane that prevents passage of eukaryotic cells.

6. The insert device according to claim 1, wherein the insert chamber is a kidney-shaped cylinder.

7. The insert device according to claim 1, wherein the first side wall follows about two thirds of the circumference of the well.

8. The insert device according to claim 7, wherein the gap protrudes inward.

9. The assembly according to 1, wherein a plurality of insert devices are joined together by neighboring flanges to form an insert tray and a plurality of wells are joined together to form a multi-well plate.

10. The assembly according to claim 9, wherein at least two of the gaps are joined to form a common gap.

11. The assembly according to claim 1, wherein the bottom of the well comprises electrodes.

12. A system for monitoring a cell culture comprising providing the assembly according to 1 coupled to a means for measuring a cell culture characteristic.

13. The system according to claim 12, wherein the bottom of the well comprises electrodes and the means for measuring the cell culture characteristic is an impedance analyzer, optionally coupled to software.

14. The system according to claim 12, wherein the means for measuring the cell culture characteristic is an optical detection device for measuring an optical property or an imaging device for producing a cell culture image.

15. A method of monitoring a cell culture comprising:
    a) providing the system according to claim 12;
    b) adding a first cell population to the well and a second cell population to the inner cavity of the insert chamber;

c) inserting the insert device into the well to form upper and lower chambers, each having separate cell populations; and d) measuring the cell culture characteristic.

16. The method according to claim 15, wherein the first population is population of target cells and the second population is a population of effector cells.

17. The method according to claim 16, wherein the cell characteristic is cell viability or cell proliferation.

18. The method according to claim 17, wherein the means for measuring the cell culture characteristic measures an optical property or an electrical property of the bottom chamber.

* * * * *